United States Patent
Anazawa

(10) Patent No.: US 11,860,094 B2
(45) Date of Patent: Jan. 2, 2024

(54) ANALYSIS SYSTEM AND ANALYSIS METHOD

(71) Applicant: HITACHI HIGH-TECHNOLOGIES CORPORATION, Tokyo (JP)

(72) Inventor: Takashi Anazawa, Tokyo (JP)

(73) Assignee: HITACHI HIGH-TECH CORPORATION, Tokyo (JP)

(*) Notice: Subject to any disclaimer, the term of this patent is extended or adjusted under 35 U.S.C. 154(b) by 0 days.

(21) Appl. No.: 16/480,333

(22) PCT Filed: Feb. 20, 2017

(86) PCT No.: PCT/JP2017/006030
§ 371 (c)(1),
(2) Date: Jul. 24, 2019

(87) PCT Pub. No.: WO2018/150559
PCT Pub. Date: Aug. 23, 2018

(65) Prior Publication Data
US 2019/0383742 A1    Dec. 19, 2019

(51) Int. Cl.
*G01N 21/64* (2006.01)
*G01N 27/447* (2006.01)
(Continued)

(52) U.S. Cl.
CPC ..... *G01N 21/6428* (2013.01); *G01N 21/6408* (2013.01); *G01N 21/6458* (2013.01);
(Continued)

(58) Field of Classification Search
CPC ........... G01N 21/6428; G01N 21/6408; G01N 21/6458; G01N 27/44782;
(Continued)

(56) References Cited

U.S. PATENT DOCUMENTS

| | | | |
|---|---|---|---|
| 2002/0009741 A1* | 1/2002 | Simpson | G01N 27/44782 435/6.16 |
| 2003/0151000 A1* | 8/2003 | Watanabe | G01N 21/6408 702/32 |

(Continued)

FOREIGN PATENT DOCUMENTS

| | | |
|---|---|---|
| CN | 1146017 A | 3/1997 |
| CN | 101464411 A | 6/2009 |

(Continued)

OTHER PUBLICATIONS

Andrade et al., "Robust normalization of DNA chromatograms by regression for improved base-calling", Journal of the Franklin Institute 341, 2004, 3-22 (Year: 2004).*

(Continued)

*Primary Examiner* — Samuel P Siefke
*Assistant Examiner* — Henry H Nguyen
(74) *Attorney, Agent, or Firm* — MATTINGLY & MALUR, PC

(57) ABSTRACT

An analysis system includes an analyzer configured to separate a sample including a plurality of components labeled with any of M kinds of fluorescent substances by chromatography and acquire first time-series data of fluorescence signals detected in N kinds (M>N) of wavelength bands in a state in which at least a part of the plurality of components is not completely separated; and a computer configured to compare the first time-series data with the second time-series data, and determine which kind of fluorescent substance of M kinds of fluorescent substances individually labels each of the plurality of components.

16 Claims, 17 Drawing Sheets

(51) Int. Cl.
*G01N 30/86* (2006.01)
*G01N 30/88* (2006.01)
*C12Q 1/68* (2018.01)

(52) U.S. Cl.
CPC ....... *G01N 27/44782* (2013.01); *G01N 30/86* (2013.01); *C12Q 1/68* (2013.01); *G01N 2021/6419* (2013.01); *G01N 2021/6421* (2013.01); *G01N 2021/6441* (2013.01); *G01N 2030/8827* (2013.01)

(58) Field of Classification Search
CPC ... G01N 2021/6419; G01N 2021/6421; G01N 2021/6441; G01N 2030/8827; G01N 2030/8831; G01N 30/86; G01N 30/74; G01N 27/447; G01N 30/88; G01N 21/64; C12N 15/00; C12Q 1/68
See application file for complete search history.

(56) References Cited

U.S. PATENT DOCUMENTS

| | | | | |
|---|---|---|---|---|
| 2003/0207310 | A1* | 11/2003 | Liu | C12Q 1/6816 435/6.1 |
| 2005/0100919 | A1* | 5/2005 | Stanton | C40B 30/04 435/6.12 |
| 2011/0256631 | A1* | 10/2011 | Tomaney | C12Q 1/6874 436/94 |
| 2013/0177913 | A1 | 7/2013 | Hasson et al. | |
| 2013/0338968 | A1* | 12/2013 | Hanashi | G01N 21/6408 702/189 |
| 2014/0336949 | A1* | 11/2014 | Yokoi | G01N 27/44782 702/20 |
| 2015/0337360 | A1 | 11/2015 | Yokoyama et al. | |

FOREIGN PATENT DOCUMENTS

| | | |
|---|---|---|
| JP | 2014-117222 A | 6/2014 |
| WO | 2015045586 A1 | 4/2015 |

OTHER PUBLICATIONS

Michael C. Giddings, et al., "A Software System for Data Analysis in Automated DNA Sequencing", Genome Res. Jun. 1998, 8: pp. 644-665.

Indu Kheterpal, et al., "A three-wavelength labeling approach for DNA sequencing using energy transfer primers and capillary electrophoresis", Electrophoresis 1998, 19, pp. 1403-1414.

International Search Report of PCT/JP2017/006030 dated May 9, 2017.

Japanese Office Action received in corresponding Japanese Application No. 2020-124810 dated Sep. 7, 2021.

Pettersson, E. et al., "Visual DNA as a Diagnostic Tool", Research Article, Electrophoresis, 2009, pp. 3691-3695.

Chinese Office Action received in corresponding Chinese Application No. 201780085297.8 dated May 6, 2022.

Search and Examination Report received in corresponding Application No. GB2117852.0 dated Jan. 14, 2022.

\* cited by examiner

FIG. 17

| SEQUENCE | BASE SPECIES | ACCURACY | QV | SEQUENCE | BASE SPECIES | ACCURACY | QV |
|---|---|---|---|---|---|---|---|
| 1 | G | 95.52% | 13.49 | 39 | A | 92.24% | 11.10 |
| 2 | T | 95.56% | 13.53 | 40 | A | 94.10% | 12.29 |
| 3 | C | 96.47% | 14.53 | 41 | C | 93.24% | 11.70 |
| 4 | G | 94.45% | 12.55 | 42 | A | 84.47% | 8.09 |
| 5 | T | 95.77% | 13.74 | 43 | A | 86.36% | 8.65 |
| 6 | C | 96.59% | 14.67 | 44 | G | 97.94% | 16.86 |
| 7 | G | 92.92% | 11.50 | 45 | T | 97.54% | 16.08 |
| 8 | T | 95.66% | 13.63 | 46 | C | 94.63% | 12.70 |
| 9 | C | 95.47% | 13.44 | 47 | G | 80.08% | 7.01 |
| 10 | G | 92.31% | 11.14 | 48 | C | 98.07% | 17.14 |
| 11 | T | 96.17% | 14.17 | 49 | C | 96.79% | 14.94 |
| 12 | C | 97.19% | 15.51 | 50 | G | 83.36% | 7.79 |
| 13 | T | 96.50% | 14.57 | 51 | T | 94.97% | 12.98 |
| 14 | T | 97.18% | 15.50 | 52 | C | 95.07% | 13.07 |
| 15 | C | 98.48% | 18.17 | 53 | A | 69.10% | 5.10 |
| 16 | T | 96.78% | 14.92 | 54 | G | 97.38% | 15.82 |
| 17 | C | 98.33% | 17.78 | 55 | T | 96.69% | 14.81 |
| 18 | C | 98.34% | 17.79 | 56 | C | 98.01% | 17.02 |
| 19 | T | 95.18% | 13.17 | 57 | T | 96.72% | 14.85 |
| 20 | C | 95.90% | 13.87 | 58 | T | 96.88% | 15.06 |
| 21 | A | 83.44% | 7.81 | 59 | C | 94.97% | 12.98 |
| 22 | C | 92.52% | 11.26 | 60 | T | 97.54% | 16.09 |
| 23 | G | 95.20% | 13.19 | 61 | T | 96.79% | 14.94 |
| 24 | T | 95.73% | 13.70 | 62 | T | 96.26% | 14.27 |
| 25 | T | 94.96% | 12.98 | 63 | G | 98.28% | 17.66 |
| 26 | C | 97.65% | 16.28 | 64 | T | 98.09% | 17.20 |
| 27 | T | 96.78% | 14.92 | 65 | C | 99.02% | 20.09 |
| 28 | C | 98.74% | 18.99 | 66 | C | 97.07% | 15.33 |
| 29 | C | 96.21% | 14.22 | 67 | T | 95.33% | 13.30 |
| 30 | A | 84.77% | 8.17 | 68 | C | 96.93% | 15.13 |
| 31 | C | 93.10% | 11.61 | 69 | C | 97.55% | 16.12 |
| 32 | T | 96.45% | 14.50 | 70 | C | 96.73% | 14.85 |
| 33 | T | 97.84% | 16.66 | 71 | G | 78.93% | 6.76 |
| 34 | C | 96.07% | 14.06 | 72 | C | 97.05% | 15.30 |
| 35 | C | 96.75% | 14.89 | 73 | G | 95.90% | 13.87 |
| 36 | T | 96.42% | 14.46 | 74 | T | 96.13% | 14.13 |
| 37 | G | 98.69% | 18.82 | 75 | C | 96.68% | 14.79 |
| 38 | T | 96.76% | 14.90 | 76 | T | 96.94% | 15.14 |
| | | | | | AVERAGE | 94.72% | 13.95 |

FIG. 18

| SEQUENCE | BASE SPECIES | ACCURACY | QV | SEQUENCE | BASE SPECIES | ACCURACY | QV |
|---|---|---|---|---|---|---|---|
| 1 | T | 95.56% | 13.53 | 39 | A | 92.24% | 11.10 |
| 2 | G | 95.52% | 13.49 | 40 | A | 94.10% | 12.29 |
| 3 | C | 96.47% | 14.53 | 41 | C | 93.24% | 11.70 |
| 4 | T | 95.77% | 13.74 | 42 | A | 84.47% | 8.09 |
| 5 | G | 94.45% | 12.55 | 43 | A | 86.36% | 8.65 |
| 6 | C | 96.59% | 14.67 | 44 | T | 97.54% | 16.08 |
| 7 | T | 95.66% | 13.63 | 45 | G | 97.94% | 16.86 |
| 8 | G | 92.92% | 11.50 | 46 | C | 94.63% | 12.70 |
| 9 | C | 95.47% | 13.44 | 47 | G | 80.08% | 7.01 |
| 10 | T | 96.17% | 14.17 | 48 | C | 98.07% | 17.14 |
| 11 | G | 92.31% | 11.14 | 49 | C | 96.79% | 14.94 |
| 12 | C | 97.19% | 15.51 | 50 | G | 83.36% | 7.79 |
| 13 | T | 96.50% | 14.57 | 51 | T | 94.97% | 12.98 |
| 14 | T | 97.18% | 15.50 | 52 | C | 95.07% | 13.07 |
| 15 | C | 98.48% | 18.17 | 53 | A | 69.10% | 5.10 |
| 16 | T | 96.78% | 14.92 | 54 | T | 96.69% | 14.81 |
| 17 | C | 98.33% | 17.78 | 55 | G | 97.38% | 15.82 |
| 18 | C | 98.34% | 17.79 | 56 | C | 98.01% | 17.02 |
| 19 | T | 95.18% | 13.17 | 57 | T | 96.72% | 14.85 |
| 20 | C | 95.90% | 13.87 | 58 | T | 96.88% | 15.06 |
| 21 | A | 83.44% | 7.81 | 59 | C | 94.97% | 12.98 |
| 22 | C | 92.52% | 11.26 | 60 | T | 97.54% | 16.09 |
| 23 | T | 95.73% | 13.70 | 61 | T | 96.79% | 14.94 |
| 24 | G | 95.20% | 13.19 | 62 | T | 96.26% | 14.27 |
| 25 | T | 94.96% | 12.98 | 63 | T | 98.09% | 17.20 |
| 26 | C | 97.65% | 16.28 | 64 | G | 98.28% | 17.66 |
| 27 | T | 96.78% | 14.92 | 65 | C | 99.02% | 20.09 |
| 28 | C | 98.74% | 18.99 | 66 | C | 97.07% | 15.33 |
| 29 | C | 96.21% | 14.22 | 67 | T | 95.33% | 13.30 |
| 30 | A | 84.77% | 8.17 | 68 | C | 96.93% | 15.13 |
| 31 | C | 93.10% | 11.61 | 69 | C | 97.55% | 16.12 |
| 32 | T | 96.45% | 14.50 | 70 | C | 96.73% | 14.85 |
| 33 | T | 97.84% | 16.66 | 71 | G | 78.93% | 6.76 |
| 34 | C | 96.07% | 14.06 | 72 | C | 97.05% | 15.30 |
| 35 | C | 96.75% | 14.89 | 73 | T | 96.13% | 14.13 |
| 36 | T | 96.42% | 14.46 | 74 | G | 95.90% | 13.87 |
| 37 | T | 96.76% | 14.90 | 75 | C | 96.68% | 14.79 |
| 38 | G | 98.69% | 18.82 | 76 | T | 96.94% | 15.14 |
|  |  |  |  |  | AVERAGE | 94.72% | 13.95 |

ANALYSIS SYSTEM AND ANALYSIS METHOD

TECHNICAL FIELD

The present invention relates to an analysis system and an analysis method.

BACKGROUND ART

Analysis methods are widely used with which a plurality of kinds of components included in samples including biological samples, such as DNA, proteins, and cells, is labeled with a plurality of kinds of fluorescent substances (where the correspondence is not always one-to-one correspondence), fluorescence emitted from the plurality of kinds of fluorescent substances is detected being identified, and hence the plurality of kinds of components is analyzed. Examples of such analysis methods include chromatography, DNA sequencing, DNA fragment analysis, flow cytometry, PCR, HPLC, Western blot, Northern blot, Southern blot, and microscopic observation.

Generally, the fluorescence spectra of a plurality of kinds of fluorescent substances have overlaps with each other (in the following, referred to as spectral overlaps). The fluorescence emissions from a plurality of kinds of fluorescent substances temporally or spatially also have overlaps with each other (in the following, referred to as space-time overlaps). In the situations in which the overlaps are present, there is a need for a technique that detects and identifies fluorescence emitted from a plurality of kinds of fluorescent substances.

Next, this technique will be described, taking an example of a DNA sequencer using electrophoresis. DNA sequencers using electrophoresis start from slab electrophoresis in 1980s, and change to methods according to capillary electrophoresis in 1990s and later. However, techniques that solve the problems do not change basically. FIG. 3 of Nonpatent Literature 1 shows a method according to slab electrophoresis. Note that the technique is also used in capillary electrophoresis. The basic processes of the technique are composed of processes (1) to (4) below under the condition M≤N.

(1) A laser beam is irradiated to a sample while being separated by electrophoresis, the sample including M kinds of DNA fragments labeled with M kinds of fluorescent substances, to make the fluorescent substances emit fluorescence, the fluorescence are detected in N colors in N kinds of wavelength bands, and hence time-series data of N color fluorescence intensities is acquired.
(2) Color conversion is applied for each time of the time-series data (1) to give time-series data of concentrations of M kinds of fluorescent substances, i.e., M kinds of DNA fragments is acquired.
(3) Correction based on the difference in the mobility of M kinds of fluorescent substances (in the following, referred to as mobility correction) is applied for each time of the time-series data (2) to give mobility-corrected time-series data of the concentrations of M kinds of fluorescent substances, i.e., M kinds of DNA fragments is acquired.
(4) Base-calling is performed based on the time-series data (3).

On the basis of the processes (1) to (4), FIG. 3 of Nonpatent Literature 1 will be described in detail. Here, M=4, N=4. In the following, the case in which a single sample is analyzed using a single electrophoresis channel will be described. In the case in which a plurality of samples is analyzed using a plurality of electrophoresis channels, the processes below are performed in parallel.

First, (1) will be described. In the preparation of a copy of DNA fragments of various lengths for a template DNA by a Sanger reaction, the DNA fragments are respectively labeled with one of four kinds of fluorescent substances corresponding to the terminal base species C, A, G, and T (in the following, for simplicity, these fluorescent substances are referred to as C, A, G, and T). A laser beam is sequentially irradiated to the DNA fragments labeled with the fluorescent substances while being separated by length through electrophoresis to make the fluorescent substances emit fluorescence. The emitted fluorescence is detected in four kinds of wavelength bands b, g, y, and r (in the following, referred to as four-color detection). The wavelength bands may correspond to the maximum emission wavelengths of C, A, G, and T. Thus, pieces of time-series data of the fluorescence intensities I(b), I(g), I(y), and I(r) of these four colors are acquired. FIG. 3A of Nonpatent Literature 1 is these pieces of time-series data (also referred to as raw data) of these colors, and I(b), I(g), I(y), and I(r) are respectively indicated by blue, green, black, and red.

Subsequently, (2) will be described. The fluorescence intensities of four colors at each time are expressed by the concentrations D(C), D(A), D(G), and D(T) of four kinds of fluorescent substances C, A, G, and T at that time as Equation (1).

[Equation 1]

$$\begin{pmatrix} I(b) \\ I(g) \\ I(y) \\ I(r) \end{pmatrix} = \begin{pmatrix} w(bC) & w(bA) & w(bG) & w(bT) \\ w(gC) & w(gA) & w(gG) & w(gT) \\ w(yC) & w(yA) & w(yG) & w(yT) \\ w(rC) & w(rA) & w(rG) & w(rT) \end{pmatrix} \begin{pmatrix} D(C) \\ D(A) \\ D(G) \\ D(T) \end{pmatrix} \quad (1)$$

Here, elements w(XY) of a four-by-four matrix W express the spectral-overlap-based intensity ratio at which a fluorescent substance Y (C, A, G, or T) is detected in a wavelength band X (b, g, y, or r). w(XY) is the fixed value determined only by the characteristics of the fluorescent substance Y (C, A, G, or T) and the wavelength band X (b, g, y, or r), and is not changed during electrophoresis.

Therefore, the concentrations of four kinds of fluorescent substances at each of the times is found from the fluorescence intensities of four colors at that time as Equation (2).

[Equation 2]

$$\begin{pmatrix} D(C) \\ D(A) \\ D(G) \\ D(T) \end{pmatrix} = \begin{pmatrix} w(bC) & w(bA) & w(bG) & w(bT) \\ w(gC) & w(gA) & w(gG) & w(gT) \\ w(yC) & w(yA) & w(yG) & w(yT) \\ w(rC) & w(rA) & w(rG) & w(rT) \end{pmatrix}^{-1} \begin{pmatrix} I(b) \\ I(g) \\ I(y) \\ I(r) \end{pmatrix} \quad (2)$$

As described above, the fluorescence intensities of four colors are multiplied by the inverse matrix $W^{-1}$, and hence the spectral overlap is solved (in the following, this process is referred to as color conversion). Thus, the concentrations of four kinds of fluorescent substances, C, A, G, and T, i.e., pieces of the time-series data of the concentrations of the DNA fragments having four kinds of bases at the ends are acquired.

FIG. 3B of Nonpatent Literature 1 is this time-series data. Color conversion is feasible regardless of the presence or absence of the space-time overlap. As shown in FIG. 3B, the presence of the concentrations of a plurality of kinds of fluorescent substances at the same time shows the presence of the space-time overlap.

FIG. 3C of Nonpatent Literature 1 is a process that corresponds none of (1) to (4), and is not necessarily performed. The time-series data in FIG. 3B is separated, by deconvolution, into individual peaks, that is, each peak expresses the concentrations of the DNA fragments of a certain length that are labeled with any one of four kinds of fluorescent substances, C, A, G, and T, and hence the space-time overlap is solved.

Lastly, (3) and (4) will be described. Generally, DNA fragments of various base lengths are separated almost at regular intervals by electrophoresis. However, the influence of the fluorescent substance with which the DNA fragment is labeled changes the mobility (electrophoresis velocity), and this sometimes makes the regular intervals unequal. Therefore, magnitude correlation of mobility according to types of fluorescent substances to be labeled is checked in advance, and time-series data in FIG. 3B or FIG. 3C of Nonpatent Literature 1 is corrected based on information on the magnitude correlation. Thus, mobility-corrected time-series data in which DNA fragments of various base lengths are arranged almost at regular intervals is acquired. FIG. 3D of Nonpatent Literature 1 is this mobility-corrected time-series data. Blue, green, black, and red peaks respectively express the concentrations of certain-length DNA fragments having the terminal base species of C, A, G, and T. In FIG. 3D, the DNA fragments are arranged in order of base lengths. Therefore, as shown in FIG. 3D, the terminal base species are arranged in order, and hence the result of base-calling can be acquired.

In the processes above, or before and after the processes, the time-series data is sometimes appropriately subjected to processing, such as smoothing, noise filtering, and base line removal.

In the color conversion process in (2), as expressed by Equation (1), the unknowns of the concentrations D(C), D(A), D(G), and D(T) of four kinds of fluorescent substances, C, A, G, and T, are found by solving four simultaneous equations composed of the known quantities of four kinds of fluorescence detection intensities I(b), I(g), I(y), and I(r) in the wavelength bands b, g, y, and r for each of the times. Generally, since this corresponds to solving M kinds of unknowns by N simultaneous equations, the condition M≤N is necessary as described above. If M>N, no solution can be uniquely found (that is, a plurality of solutions is possibly present), and hence color conversion (Equation (2)) is unfeasible.

However, in Nonpatent Literature 2, DNA sequencing by electrophoresis is addressed under the condition M>N where M=4, N=3. The emission of fluorescence is detected in three kinds of wavelength bands b, g, and r (in the following, referred to as three-color detection), and then the fluorescence intensities in four colors at each time in Equation (1) are substituted for three color fluorescence intensities at each time in Equation (3).

[Equation 3]

$$\begin{pmatrix} I(b) \\ I(g) \\ I(r) \end{pmatrix} = \begin{pmatrix} w(bC) & w(bA) & w(bG) & w(bT) \\ w(gC) & w(gA) & w(gG) & w(gT) \\ w(rC) & w(rA) & w(rG) & w(rT) \end{pmatrix} \begin{pmatrix} D(C) \\ D(A) \\ D(G) \\ D(T) \end{pmatrix} \quad (3)$$

At this time, the matrix W has three rows and four columns, and has no inverse matrix. Thus, none of the concentrations of four kinds of fluorescent substances can be uniquely found unlike Equation (2). As described above, generally, no solution can be found under the condition M>N. However, a solution can be found by additionally providing preconditions as below.

In the first step, it is assumed that there is no space-time overlap in a plurality of kinds of fluorescent substances, i.e., it is assumed that only one kind of fluorescent substance emits fluorescence at a time. At this time, Y (C, A, G, or T) at which the ratio of three color fluorescence intensities (I(b) I(g) I(r))$^T$ and the ratio of four columns (w(bY) w(gY) w(rY))$^T$ of the matrix W are the closest at each of the times can be selected. In other words, when one kind of fluorescent substance is selected in Equation (3) and the concentrations of the remaining three kinds of fluorescent substances is zero, i.e., when (D(C) D(A) D(G) D(T))$^T$ is (D(C) 0 0 0)$^T$, (0 D(A) 0 0)$^T$, (0 0 D(G) 0)$^T$, or (0 0 0 D(T))$^T$, D(Y) (Y is C, A, G, or T) where the difference between the left-hand side and the right-hand side is the smallest is individually found. Thus, Y (C, A, G, or T) at which the difference between the left-hand side and the right-hand side at this time is the smallest can be selected. Here, in the case in which the difference between the left-hand side and the right-hand side is not sufficiently small in any case, the process goes to the subsequent second step.

In the second step, it is assumed that only two kinds of fluorescent substances emit fluorescence at a time. Now, when two kinds of fluorescent substances are selected in Equation (3) and the concentrations of the remaining two kinds of fluorescent substances is zero, i.e., when (D(C) D(A) D(G) D(T))$^T$ is (D(C) D(A) 0 0)$^T$, (D(C) 0 D(G) 0)$^T$, (D(C) 0 0 D(T))$^T$, (0 D(A) D(G) 0)$^T$, (0 D(A) 0 D(T))$^T$, or (0 0 D(G) D(T))$^T$, two kinds of D(Y) (Y is C, A, G, or T) where the difference between the left-hand side and the right-hand side is the smallest are individually found. Two kinds of Y (C, A, G, or T) where the difference between the left-hand side and the right-hand side at this time is the smallest can be selected.

In this manner, similarly to the process (2) in Nonpatent Literature 1, the time-series data of the concentrations of four kinds of fluorescent substances, i.e., four kinds of DNA fragments, is acquired. After that, processes equivalent to processes (3) and (4) in Nonpatent Literature 1 are performed, and hence the result of base-calling can be acquired.

In order to hold the conditions of performing the first and the second steps in Nonpatent Literature 2, i.e., the assumption that only one kind or two kinds of fluorescent substances emit fluorescence at a time, it is necessary to hold a small space-time overlap, i.e., two conditions below.

(a) In the time-series data of the concentrations of four kinds of DNA fragments, a plurality of peaks derived from the DNA fragments of certain lengths is arranged almost at regular intervals.

(b) In the time-series data of the concentrations of four kinds of DNA fragments, two adjacent peaks derived from the DNA fragments of two kinds of base lengths differed by one base length are excellently separated.

In Nonpatent Literature 2, four kinds of primers used in the Sanger reaction are labeled with four kinds of fluorescent substances different from each other (precisely, a labeling method for three kinds of fluorescent substances is modified), and the difference in mobility due to the influence of the fluorescent substance with which the DNA fragment is labeled is made sufficiently small. In addition, the condition in which electrophoresis separation performance is sufficiently high is satisfied. That is, the time-series data of the three-color fluorescence intensity $(I(b)\ I(g)\ I(r))^T$ where the assumptions (a) and (b) are held is acquired (the upper part of FIG. 2 in Nonpatent Literature 2). Under these conditions, the first and the second steps are performed. Thus, the time-series data of the concentrations of four kinds of fluorescent substances, i.e., four kinds of DNA fragments, is acquired, and the result of base-calling is obtained (the lower part of FIG. 2 in Nonpatent Literature 2).

CITATION LIST

Nonpatent Literature

Nonpatent Literature 1: Genome Res. pp. 644-65, 8(6), June 1998

Nonpatent Literature 2: Electrophoresis. pp. 1403-14, 19(8-9), June 1998

SUMMARY OF INVENTION

Technical Problem

An RGB color sensor is a two-dimensional sensor having three kinds of pixels arrayed, the sensor being configured to detect the wavelength bands of red (R), green (G), and blue (B) corresponding to three primary colors that human eyes can identify. The RGB color sensor is used not only in single-lens reflex digital cameras and compact digital cameras but also in digital cameras installed on smartphones these years, and is explosively popular in the world. Thus, the performance is remarkably improved, and the price is also remarkably decreased. Therefore, it is extremely useful that the RGB color sensor is applied to the analysis method in which fluorescence emitted from the plurality of kinds of fluorescent substances is detected while being identified and a plurality of kinds of components is detected. However, since the RGB color sensor can detect only three colors, it is difficult to identify the emissions of fluorescence from four kinds or more fluorescent substances. As described above, generally, in order to identify the emissions of fluorescence from M kinds of fluorescent substances, in the case in which M kinds of fluorescent substances have a spectral overlap and a space-time overlap, N-color detection has to be performed in N kinds of wavelength bands where the condition M≤N is satisfied.

Nonpatent Literature 2 solves the problem in the case in which the emissions of fluorescence from M=four kinds of fluorescent substances is detected in N=three colors on the DNA sequencer using electrophoresis (that is, M>N) by providing preconditions on the space-time overlap. These are the conditions in which only one kind or two kinds of fluorescent substances emit fluorescence at a time, i.e., the conditions (a) and (b) are held.

However, generally, the conditions (a) and (b) are not held in many cases. Also in the time-series data of three color fluorescence intensities (upper) and the time-series data of the concentrations of four kinds of fluorescent substances (lower) in FIG. 2 of Nonpatent Literature 2, in the regions indicated by asterisks, although electrophoresis separation performance, three or more peaks respectively derived from the DNA fragments of certain lengths are crowded due to a phenomenon referred to as compression. Thus, the condition (a) is not held, and hence correct base-calling is not achieved. In the closing stage of electrophoresis in FIG. 2 of Nonpatent Literature 2, the electrophoresis separation performance is reduced. Therefore, because separation of two adjacent peaks derived from the DNA fragments of two kinds of base lengths differed by one base length is insufficient, the condition (b) is not held, and hence correct base-calling is not achieved.

In Nonpatent Literature 2, the condition (a) is achieved using a primer labeling method in which four kinds of primers used in the Sanger reaction are labeled with four kinds of fluorescent substances different from each other. However, nowadays, instead of the primer labeling method, a terminator labeling method in which four kinds of terminators used in the Sanger reaction are labeled with four kinds of different fluorescent substances is mainly used. In the primer labeling method, it is necessary to separately perform the Sanger reaction using four kinds of primers, i.e., in four different sample tubes. On the other hand, in the terminator labeling method, the Sanger reaction using four kinds of terminators can be performed together, i.e., in one sample tube. Therefore, the terminator labeling method can greatly simplify the Sanger reaction.

However, in the primer labeling method, the difference in mobility of DNA fragments labeled with four kinds of fluorescent substances is small, whereas in the terminator labeling method, the difference in mobility of DNA fragments labeled with four kinds of fluorescent substances is large, and hence the condition (a) is not held inevitably. That is, only one kind or two kinds of fluorescent substances do not necessarily emit fluorescence, and there is a possibility that three kinds or more fluorescent substances sometimes emit fluorescence at a time. Therefore, in the case in which at least the terminator labeling method is used, it is difficult to perform DNA sequencing by the method of Nonpatent Literature 2.

Therefore, the present invention is to provide an analysis technique to detect M kinds of components by N-color detection in N kinds (M>N) of wavelength bands in the state in which fluorescence emitted from M kinds of fluorescent substances has a spectral overlap and a space-time overlap.

Solution to Problem

For example, in order to solve the problem, configurations described in claims are adopted. The present application includes multiple schemes that solve the problem. For an example, there is provided an analyzer configured to separate a sample including a plurality of components labeled with any of M kinds of fluorescent substances by chromatography and acquire first time-series data of fluorescence signals detected in N kinds (M>N) of wavelength bands in a state in which at least a part of the plurality of components is not completely separated; a storage unit configured to store second time-series data of individual model fluorescence signals of the plurality of components; and a computer configured to compare the first time-series data with the second time-series data, and determine that which kinds of fluorescent substances of the M kinds of fluorescent substances individually label the plurality of components.

According to another example, there is provided an analysis method comprising: separating a sample including a plurality of components labeled with any of M kinds of fluorescent substances by chromatography to acquire first time-series data of fluorescence signals detected in N kinds (M>N) of wavelength bands in a state in which at least a part of the plurality of components is not completely separated; and determining that which kinds of fluorescent substances of the M kinds of fluorescent substances individually label the plurality of components by comparing the first time-series data with second time-series data of individual model fluorescence signals of the plurality of components.

Advantageous Effects of Invention

According to the present invention, M kinds of components can be detected even in M>N in the state in which fluorescence emitted from M kinds of fluorescent substances has a spectral overlap and a space-time overlap. Note that further characteristics relating to the present invention will be apparent from the description of the present specification and the accompanying drawings. Problems, configurations, and effects other than those described above will be apparent from the description of embodiments below.

BRIEF DESCRIPTION OF DRAWINGS

FIG. 17 is a diagram collecting the terminal base species, the fitting accuracy, and the QV (Quality Value) for model peaks in FIG. 15 (5) in the temporal order of electrophoresis.
FIG. 18 is a diagram collecting the terminal base species, the fitting accuracy, and the QV for model peaks in FIG. 15 (6) in the temporal order of electrophoresis after correction.

DESCRIPTION OF EMBODIMENTS

In the following, embodiments of the present invention the will be described with reference to the accompanying drawings. Note that the accompanying drawings illustrate specific embodiments according to the principle of the present invention. However, these drawings are provided for understanding the present invention, and are not used for limitedly interpreting the present invention at all.

The embodiments below relate to a device that detects fluorescences, being identified, from a sample including a plurality of components labeled with a plurality of fluorescent substances and hence analyzes the components. The embodiments below are applicable to the fields of chromatography, DNA sequencing, DNA fragment analysis, flow cytometry, PCR, HPLC, Western blot, Northern blot, Southern blot, microscopic observation, and any other method, for example.

In the case in which DNA sequencing by electrophoresis is performed, the content of Nonpatent Literatures 1 and 2 will be described in more detail using FIGS. 1 to 4.

Figure 1:
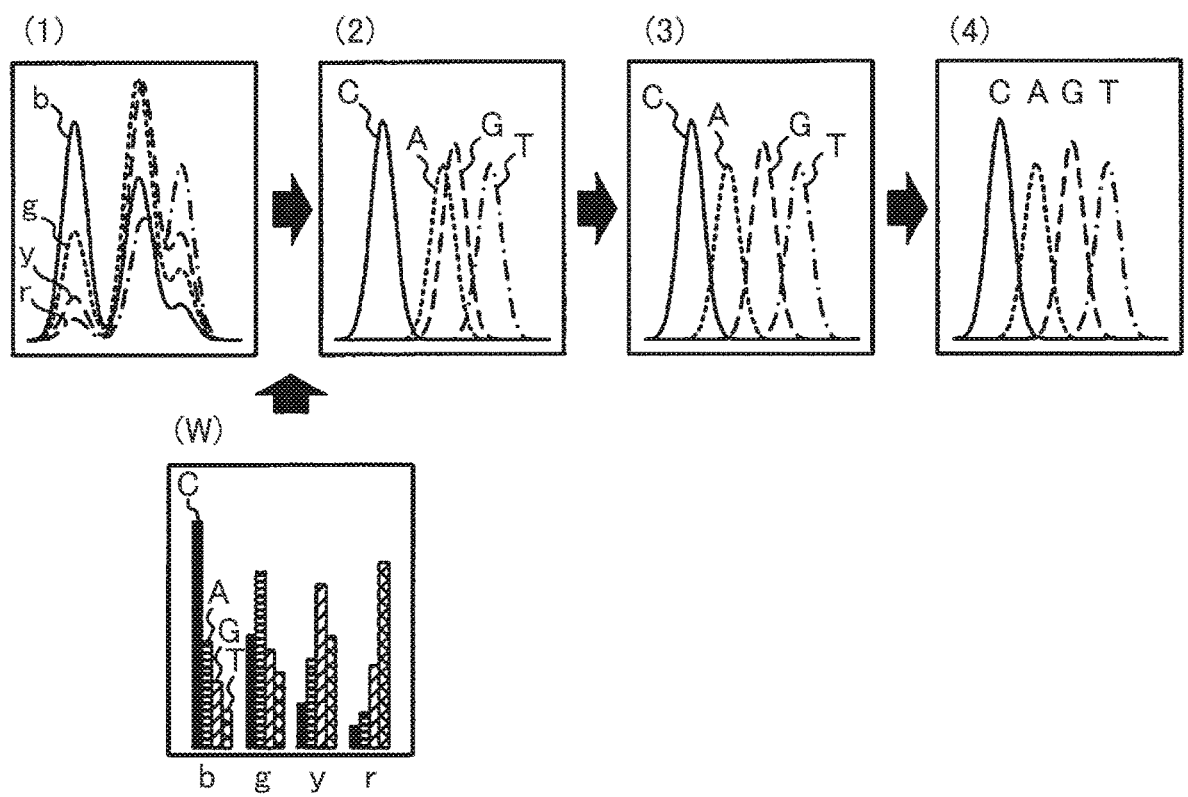
FIG. 1 is a diagram showing a DNA sequencing method according to Nonpatent Literature 1 using model data.

FIG. 1 shows a method of Nonpatent Literature 1. FIG. 1 (1) shows time-series data of four color fluorescence intensities I(b), I(g), I(y), and I(r) obtained by four-color detection of the emissions of fluorescence from four kinds of fluorescent substances C, A, G, and T in four kinds of wavelength bands b, g, y, and r. The horizontal axis in FIG. 1 expresses time, and the vertical axis expresses fluorescence intensity.

FIG. 1 (W) shows elements w(XY) in four row and four columns of a matrix W. For example, four black bar graphs express w(bC), w(gC), w(yC), and w(rC) from the left. Similarly, horizontal stripe bar graphs express w(XA) (X is b, g, y, and r), oblique stripe bar graph express w(XG) (X is b, g, y, and r), and check bar graphs express w(XT) (X is b, g, y, and r). The graphs w(bY), w(gY), w(yY), and w(rY) are normalized such that w(bY)+w(gY)+w(yY)+w(rY)=1 (Y is C, A, G, or T).

Specifically, the matrix W and the inverse matrix $W^{-1}$ of the matrix W are as follows.

[Equation 4]

$$W = \begin{pmatrix} w(bC) & w(bA) & w(bG) & w(bT) \\ w(gC) & w(gA) & w(gG) & w(gT) \\ w(yC) & w(yA) & w(yG) & w(yT) \\ w(rC) & w(rA) & w(rG) & w(rT) \end{pmatrix} = \begin{pmatrix} 0.56 & 0.26 & 0.16 & 0.09 \\ 0.28 & 0.43 & 0.24 & 0.18 \\ 0.11 & 0.22 & 0.40 & 0.27 \\ 0.06 & 0.09 & 0.20 & 0.45 \end{pmatrix} \quad (4)$$

$$W^{-1} = \begin{pmatrix} w(bC) & w(bA) & w(bG) & w(bT) \\ w(gC) & w(gA) & w(gG) & w(gT) \\ w(yC) & w(yA) & w(yG) & w(yT) \\ w(rC) & w(rA) & w(rG) & w(rT) \end{pmatrix}^{-1} = \begin{pmatrix} 2.55 & -1.44 & -0.27 & 0.23 \\ -1.76 & 4.27 & -1.68 & -0.34 \\ 0.33 & -2.12 & 4.64 & -2.00 \\ -0.12 & 0.29 & -1.69 & 3.12 \end{pmatrix} \quad (5)$$

I(b), I(g), I(y), and I(r) at each time in FIG. 1 (1) is multiplied by the inverse matrix $W^{-1}$ of the matrix W (i.e., by color conversion), and hence the time-series data of the concentrations D(C), D(A), D(G), and D(T) of four kinds of fluorescent substances C, A, G, and T, i.e., four kinds of DNA fragments having base species C, A, G, and T at the ends is acquired as shown in FIG. 1 (2).

In FIG. 1 (2), four peaks of C, A, G, and T are obtained. The heights of the peaks, i.e., the concentrations (arbitrary unit), are D(C)=100, D(A)=80, D(G)=90, and D(T)=80. The times (arbitrary unit) of the peaks are 30, 55, 60, and 75.

Although the peak of A and the peak of G have a large space-time overlap with each other, color conversion can correctly find each of the concentrations even in this case.

FIG. 1 (3) shows mobility-corrected time-series data of the concentrations D(C), D(A), D(G), and D(T) of four kinds of fluorescent substances or DNA fragments, obtained by compensating the differences in mobility due to the kinds of fluorescent substances to be labeled that is checked in advance in the results in FIG. 1 (2). Specifically, since it is known that the mobility of the DNA fragments labeled with the fluorescent substance A is decreased with respect to the mobilities of the DNA fragments labeled with the other fluorescent substances so that the peak-detection time of the DNA fragments labeled with the fluorescent substance A is delayed by a duration (arbitrary unit) of 10 with respect to the peak-detection time of the DNA fragments labeled with the other fluorescent substances. Therefore, mobility correction is performed in which the peak-detection time of the DNA fragments labeled with the fluorescent substance A is preceded by 10. That is, the detection time (of the peak of A is corrected from 55 to 45 in FIG. 1 (2). As a result of this mobility correction, time-series data is acquired in which DNA fragments of various base lengths are arranged almost at regular intervals.

FIG. 1 (4) shows results of base-calling performed based on FIG. 1 (3). It is fine that the labeling fluorescent substance species to which the peaks belong or the terminal base species of the DNA fragments are read in temporal order.

Figure 2:
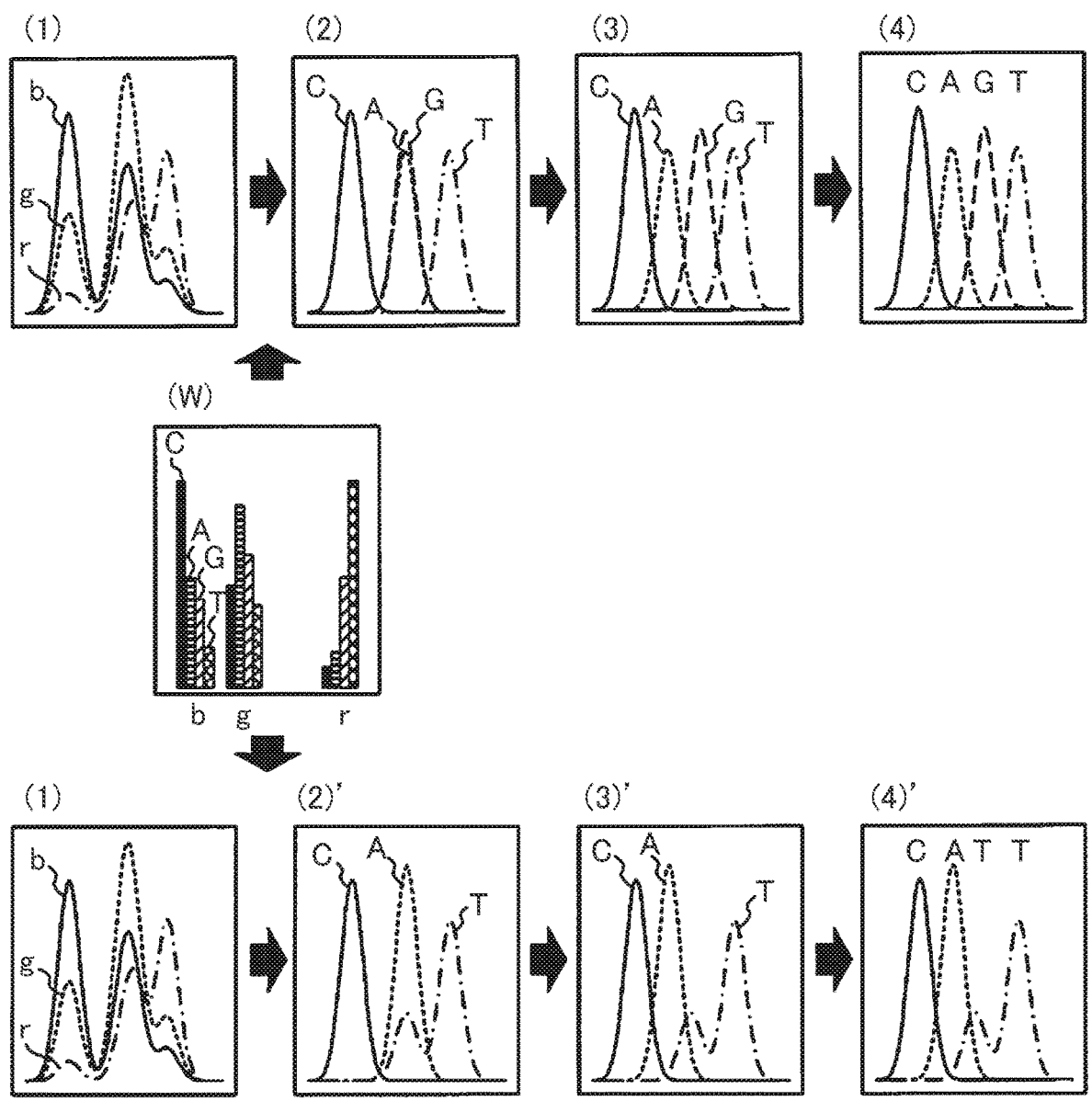
FIG. 2 is a diagram showing a DNA sequencing method according to Nonpatent Literature 2 using model data.

FIG. 2 shows a method of Nonpatent Literature 2. FIG. 2 (1) shows time-series data of three color fluorescence intensities I(b), I(g), and I(r) obtained by three-color detection of the emissions of fluorescence from four kinds of fluorescent substances C, A, G, and T in three kinds of wavelength bands b, g, and r.

In FIG. 2 (1), only the time-series data of I(y) is removed from FIG. 1 (1), and the time-series data of I(b), I(g), and I(r) are the same in both drawings.

FIG. 2 (W) shows elements w(XY) in three rows and four columns of a matrix W. For example, four black bar graphs express w(bC), w(gC), and w(rC) from the left. Similarly, horizontal stripe bar graphs express w(XA) (X is b, g, and r), oblique stripe bar graphs express w(XG) (X is b, g, and r), and check bar graphs express w(XT) (X is b, g, and r). w(bY), w(gY), and w(rY) are normalized such that w(bY)+w(gY)+w(rY)=1 (Y is C, A, G, or T).

Specifically, the matrix W is as follows.

[Equation 5]

$$W = \begin{pmatrix} w(bC) & w(bA) & w(bG) & w(bT) \\ w(gC) & w(gA) & w(gG) & w(gT) \\ w(rC) & w(rA) & w(rG) & w(rT) \end{pmatrix} = \begin{pmatrix} 0.63 & 0.33 & 0.27 & 0.13 \\ 0.31 & 0.56 & 0.40 & 0.25 \\ 0.06 & 0.11 & 0.33 & 0.63 \end{pmatrix} \quad (6)$$

As the first step, the case is considered in FIG. 2 (1) in which only one kind of fluorescent substance emits fluorescence at a time using FIG. 2 (W). In FIG. 2 (1), two peaks observed on the left side and the right side have ratios of the three-color fluorescence intensity $(I(b)\ I(g)\ I(r))^T$ close to the ratios of $(0.63\ 0.31\ 0.06)^T$ and $(0.13\ 0.25\ 0.63)^T$, respectively. Thus, these two peaks can be determined as single peaks of C and T. The heights of the peaks of these C and T, i.e., the concentrations (arbitary unit), are D(C)=100 and D(T)=80, and the times (arbitrary unit) of the peaks of these C and T are 30 and 75, respectively.

On the other hand, the peak observed in the center of FIG. 2 (1) has a ratio of the three-color fluorescence intensity $(I(b)\ I(g)\ I(r))^T$ that is not close to any ratio of $(w(bY)\ w(gY)\ w(rY))^T$ (Y is C, A, G, or T). Therefore, as the second step, the case is considered in which only two kinds of fluorescent substances emit fluorescence at a time using FIG. 2 (W). Here, the solution that the peaks of A and G are detected at the same time can be derived. Specifically, when the heights of the peaks, i.e., the concentrations (arbitrary unit) are D(A)=80 and D(G)=90 and the times (arbitrary unit) of the peaks are 55 and 55, the difference between the left-hand side and the right-hand side in Equation (3) is decreased, and hence the peaks observed in the center of FIG. 2 (1) can be explained. From the results above, time-series data of the concentrations D(C), D(A), D(G), and D(T) of four kinds of fluorescent substances C, A, G, and T, i.e., four kinds of DNA fragments having base species C, A, G, and T at the ends is acquired as shown in FIG. 2 (2).

Similarly to FIG. 1 (3), FIG. 2 (3) shows mobility-corrected time-series data of the concentrations D(C), D(A), D(G), and D(T) of four kinds of fluorescent substances or DNA fragments. The detection time (arbitrary unit) of the peak of A is preceded by 10, and corrected from 55 to 45. In order to align the peak intervals, the detection time (arbitrary unit) of the peak of G is moved backward by five, and corrected from 55 to 60. As a result, FIG. 2 (3) and FIG. 1 (3) are the same. FIG. 2 (4) shows results of base-calling similarly to FIG. 1, and the same as FIG. 1 (4).

On the other hand, FIG. 2 shows that processes from FIG. 2 (1) to FIG. 2 (2) are not determined in a certain manner. Although the first step is the same as the processes above, in the second step, another solution is derived, and FIG. 2 (2)' is obtained, instead of FIG. 2 (2). That is, the solution that the peaks of A and T are detected at the same time can be derived. Specifically, when the heights of the peaks, i.e., the concentrations (arbitrary unit) are D(A)=107 and D(T)=34 and the times (arbitrary unit) of the peaks are 55 and 55, the difference between the left-hand side and the right-hand side in Equation (3) is decreased, and hence the peak observed in the center of FIG. 2 (1) can be explained. From the results above, time-series data of the concentrations D(C), D(A), D(G), and D(T) of four kinds of fluorescent substances C, A, G, and T, i.e., four kinds of DNA fragments having base species C, A, G, and T at the ends is acquired as shown in FIG. 2 (2)'.

However, in FIG. 2 (2)', because G is not detected, D(G)=0. Similarly to FIG. 1 (3), FIG. 2 (3)' shows mobility-corrected time-series data of the concentrations D(C), D(A), D(G), and D(T) of four kinds of fluorescent substances or DNA fragments. The detection time (arbitrary unit) of the peak of A is preceded by 10, and corrected from 55 to 45. FIG. 2 (4)' shows results of base-calling performed based on FIG. 2 (3)'. Although the same FIG. 2 (1) and FIG. 2 (W) are used, FIG. 2 (2), FIG. 2 (3), and FIG. 2 (4) are totally different from FIG. 2 (2)', FIG. 2 (3)', and FIG. 2 (4)', and different base-calling results are derived. In the model data used here, since the base-calling results shown in FIG. 1 (4) is a positive solution, FIG. 2 (4) shows correct base-calling results, but FIG. 2 (4)' shows wrong base-calling results.

Therefore, in the method of Nonpatent Literature 2, a plurality of solutions are possibly derived from the same measured results, and there is a risk that wrong base-calling results are derived, generally, wrong analysis results.

First Embodiment

Figure 3:
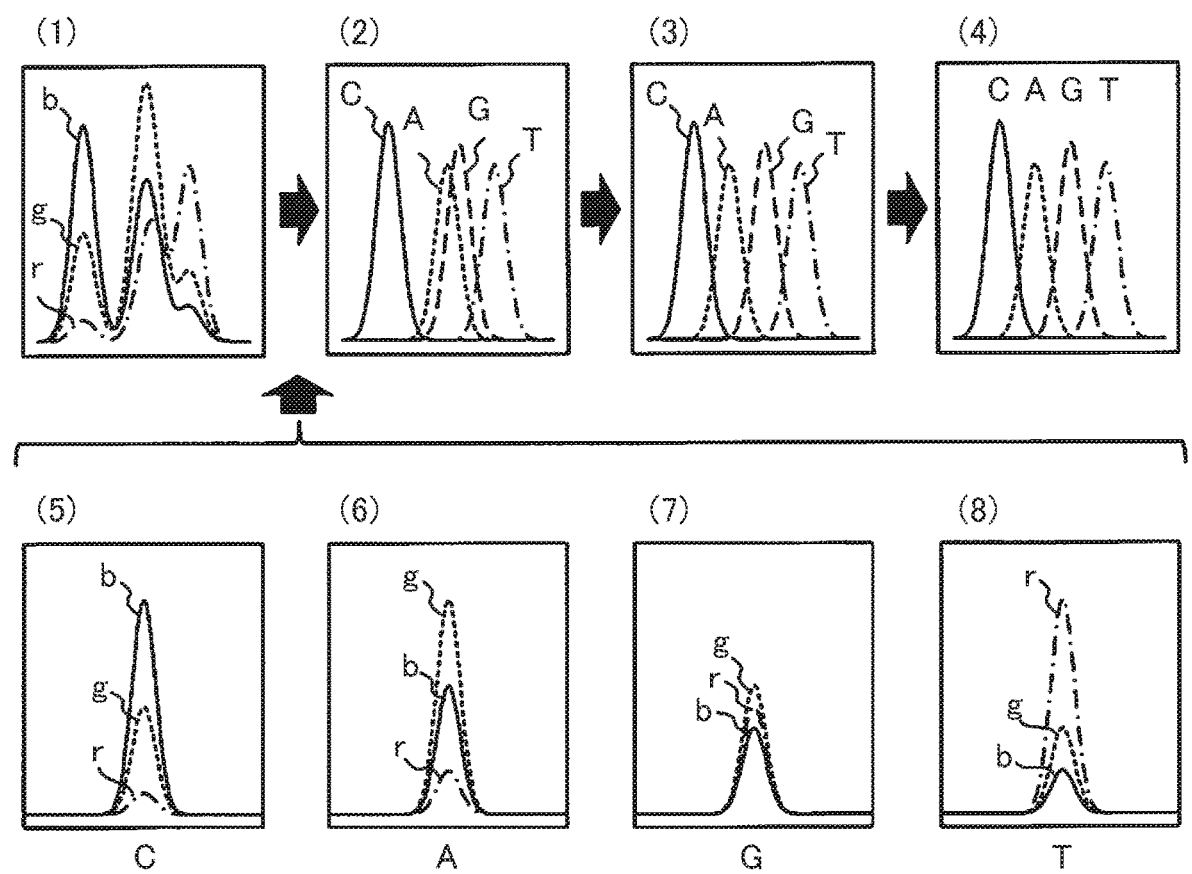
FIG. 3 is a diagram showing an example of a DNA sequencing method using model data according to a first embodiment.

FIG. 3 is a diagram showing a DNA sequencing method using model data according to a first embodiment. FIG. 3 (1)

shows time-series data of three color fluorescence intensities I(b), I(g), and I(r) obtained by three-color detection of the emissions of fluorescence from four kinds of fluorescent substances C, A, G, and T in three kinds of wavelength bands b, g, and r, which is the same as FIG. 2 (1).

FIG. 3 (5) shows time-series data of the three color fluorescence intensities I(b), I(g), and I(r) of a model peak obtained when DNA fragments of a certain length labeled with the fluorescent substance C are detected in three colors. The vertical axis in FIG. 3 (5) expresses the fluorescence intensity, and the horizontal axis is time. The data in FIG. 3 (5) expresses a temporal change in fluorescence intensity of the model peaks of three fluorescence colors (b, g, and r) when the DNA fragments of the certain length labeled with the fluorescent substance C are detected. Here, the three-color fluorescence intensity ratio at any time is (w (bC) w(gC) w(rC))$^T$=(0.63 0.31 0.06)$^T$ of the matrix W in Equation (6). Similarly, FIGS. 3 (6), (7), and (8) show time-series data of the three color fluorescence intensities I(b), I(g), and I(r) of model peaks when DNA fragments of certain lengths labeled with the fluorescent substances A, G, and T are detected in three colors. The three color fluorescence intensity ratios in FIGS. 3 (6), (7), and (8) are respectively (0.33 0.56 0.11)$^T$, (0.27 0.40 0.33)$^T$, (0.13 0.25 0.63)$^T$.

The shape of each of the model peaks is Gaussian here, and dispersion of the Gaussian distribution is matched with spatial dispersion of the DNA fragments of a certain base length observed in experiments. Note that the shapes of the model peaks are non-limiting to this example, and the shapes of the model peaks may have other configurations. Here, the model peaks in FIGS. 3 (5), (6), (7), and (8) are fitted to the time-series data of FIG. 3 (1) only by changing heights and times of the model peaks. An example of the fitting process will be described with reference to FIG. 3. For example, the fitting process is executed in a stepwise fashion from the left end of the data of FIG. 3 (1). For example, height (fluorescence intensity) and median (electrophoresis time) of the Gaussian distribution in FIG. 3 (5) are varied to minimize difference between the fitted curve (the varied Gaussian distribution) and the time-series data of FIG. 3(1). Then the fitting is achieved when the difference is smaller than a predetermined error. That is, here, the fitting is determined when fluorescence intensity and electrophoresis time of the fitted curve are most matched to those of the time-series data of FIG. 3(1). Note that the fitting may be performed while width of the Gaussian distribution is also changed. In the case in which no fitting is achieved by the Gaussian distribution in FIG. 3 (5), it is determined whether fitting is achieved using other data (Gaussian distribution in FIGS. 3 (6), (7), and (8)) or the combination of other data. As described above, fitting to the data of FIG. 3 (1) is performed using any data of FIGS. 3 (5), (6), (7), and (8) or these combination of these pieces of data. The error in the fitting process can be calculated based on the difference between the peak shapes of FIG. 3 (1) and the shapes of the fitted model peaks, for example. Various publicly known methods may be applied to calculating the error. Note that from the viewpoint of efficiency, preferably, fitting is performed in a stepwise manner from the end of the data of FIG. 3 (1), for example. This is because since tail of an adjacent peak of fluorescence leaks into a certain peak of fluorescence, performing fitting from the end of data efficiently enables fitting in consideration of the leakage of the adjacent peak.

FIG. 3 (2) shows results of performing the fitting process. At this time, the peak shape of C is time-series data that the height of the time-series data of I(b) is multiplied by 1/w(bC)=1/0.63=1.59. The peak shape of A is time-series data that the height of the time-series data of I(g) is multiplied by 1/w(gA)=1/0.56=1.79. The shape peak of G is time-series data that the height of the time-series data of I(g) is multiplied by 1/w(gG)=1/0.40=2.50. The peak shape of T is time-series data that the height of the time-series data of I(r) is multiplied by 1/w(rT)=1/0.63=1.59.

Based on these results, FIG. 3 (2) is the same as FIG. 1 (2). A method of acquiring FIGS. 3 (3) and (4) further is similar to the method of acquiring FIGS. 1 (3) and (4). According to the embodiment, since the process that derives FIG. 3 (2) from FIG. 3 (1) is uniquely determined, correct base-calling results can be acquired as shown in FIG. 3 (4).

In the method of Nonpatent Literature 2 in FIG. 2, in deriving FIG. 2 (2) or FIG. 2 (2)' from FIG. 2 (1), only the matrix W shown in Equation (6), i.e., the three-color fluorescence detection intensity ratios of the emissions of fluorescence from the fluorescent substances are used. On the other hand, in the embodiment shown in FIG. 3, in deriving FIG. 3 (2) from FIG. 3 (1), the peak shapes of the emissions of fluorescence from the fluorescent substances, i.e., temporal change information is used, in addition to the matrix W shown in Equation (6), i.e., the three-color fluorescence detection intensity ratios of the emissions of fluorescence from the fluorescent substances. These differences cause the difference whether the solution can be uniquely derived, i.e., correct base-calling results can be obtained.

Figure 4:
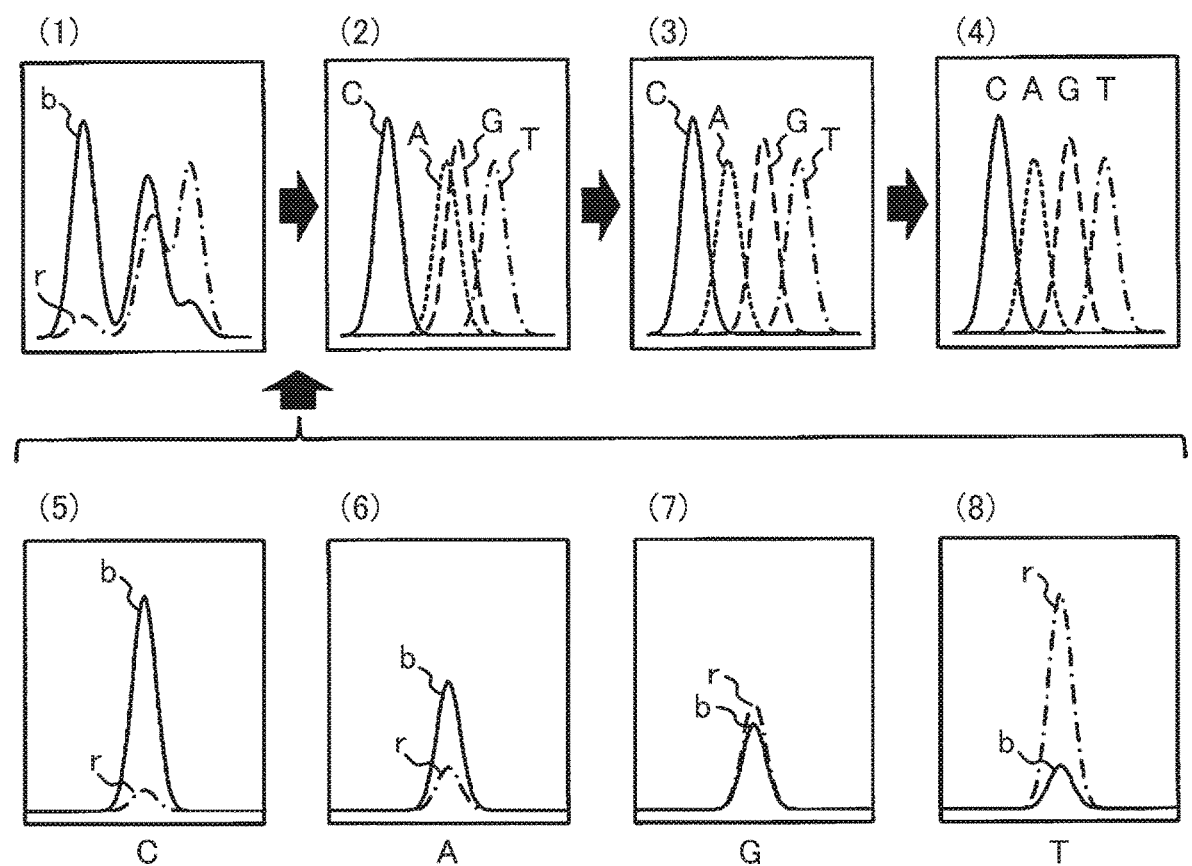
FIG. 4 is a diagram showing another example of a DNA sequencing method using model data according to the first embodiment.

FIG. 4 shows an example of the case in which three-color detection performed in FIG. 3 is further limited to two-color detection. FIG. 4 (1) shows time-series data of two color fluorescence intensities I(b) and I(r) obtained by two-color detection of the emissions of fluorescence from four kinds of fluorescent substances C, A, G, and T in two kinds of wavelength bands b and r, and is the time-series data in FIG. 3 (1) from which the time-series data of I(g) is removed.

FIG. 4 (5) shows time-series data of the two color fluorescence intensities I(b) and I(r) of a model peak when DNA fragments in a certain length labeled with the fluorescent substance C are detected in two colors, and is the time-series data in FIG. 3 (5) from which the time-series data of I(g) is removed. Similarly, FIGS. 4 (6), (7), and (8) are time-series data of the two color fluorescence intensities I(b) and I(r) of model peaks when DNA fragments in certain lengths labeled with the fluorescent substances A, G, and T are detected in two colors, and are the time-series data that the time-series data in FIGS. 3 (6), (7), and (8) from which I(g) is removed.

Here, the model peaks in FIGS. 4 (5), (6), (7), and (8) are fitted to the time-series data of FIG. 4 (1) only by changing heights and times of the model peaks. FIG. 4 (2) shows the results of performing the fitting process. At this time, the peak shape of C is time-series data that the height of the time-series data of I(b) is multiplied by 1/w(bC)=1/0.63=1.59. The peak shape of A is time-series data that the height of the time-series data of I(b) is multiplied by 1/w(bA)=1/0.33=3.03. The shape peak of G is time-series data that the height of the time-series data of I(r) is multiplied by 1/w(rG)=1/0.33=3.03. The peak of T is time-series data that the height of the time-series data of I(r) is multiplied by 1/w(rT)=1/0.63=1.59.

Based on these results, FIG. 4 (2) is the same as FIG. 1 (2). A method of further acquiring FIGS. 4 (3) and (4) is similar to the method of acquiring FIGS. 1 (3) and (4). According to the embodiment, since the process that derives FIG. 4 (2) from FIG. 4 (1) is uniquely determined, correct base-calling results can be acquired as shown in FIG. 4 (4).

Figure 5:
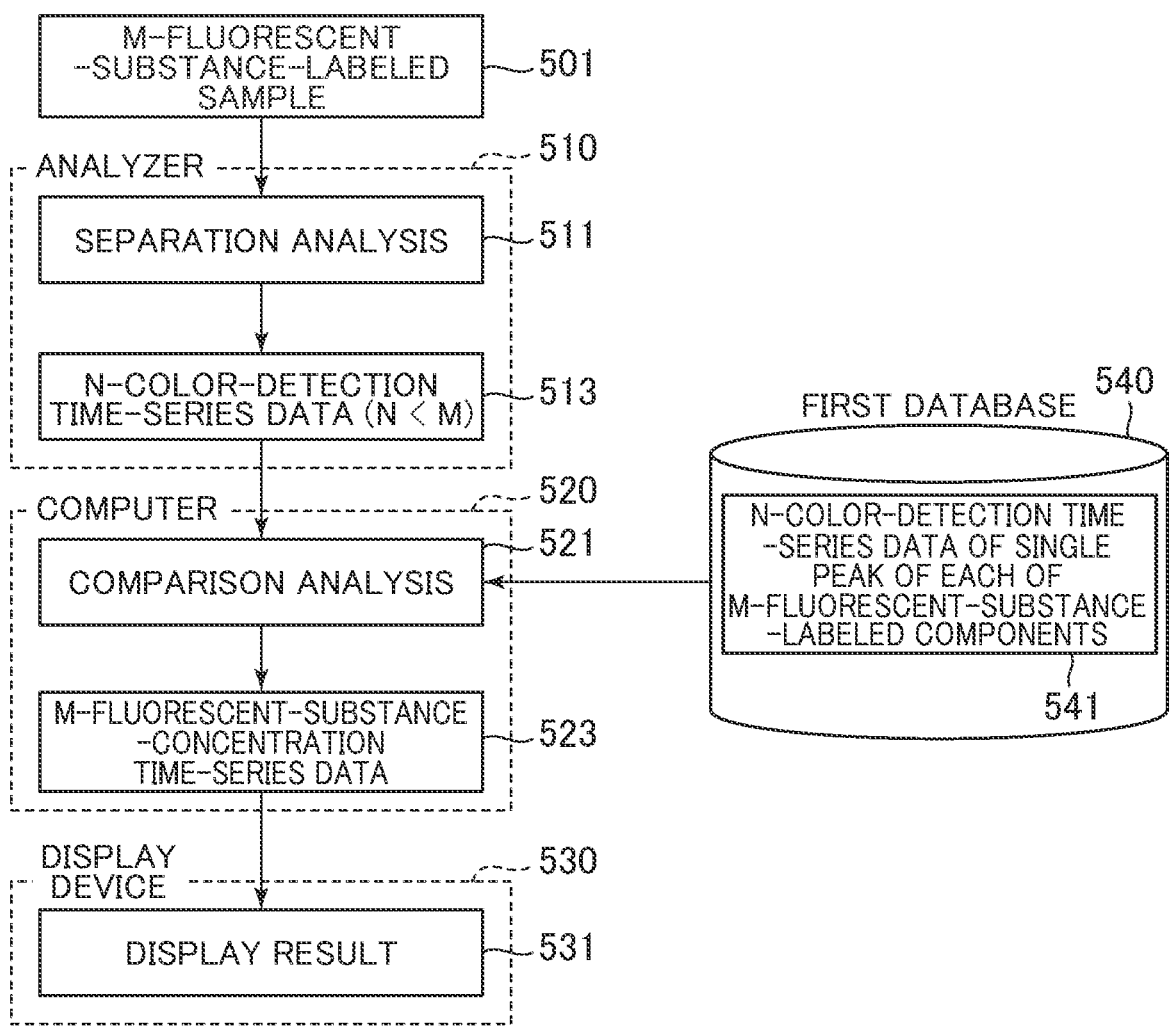
FIG. 5 is a diagram showing process steps and the configuration of a system according to the first embodiment.

FIG. 5 shows process steps and a configuration of a system according to the embodiment. The system according to the first embodiment includes an analyzer 510, a computer 520, and a display device 530. The analyzer 510 is a liquid chromatography device, for example. The computer 520 may be achieved using a general-purpose computer, for example. The processing unit of the computer 520 may be achieved as the functions of programs executed on a computer. The computer at least includes a processor, such as a CPU (Central Processing Unit), and a storage unit, such as a memory. The process of the computer 520 may be achieved in which the processes corresponding to program codes are stored in the memory and the processor executes the program codes.

In this configuration, the analyzer 510 separates a sample including a plurality of components labeled with any of M kinds of fluorescent substances (M-fluorescent-substance-labeled sample 501) by chromatography, and acquires first time-series data of fluorescence signal detected in N kinds (M>N) of wavelength bands in a state in which at least a part of the plurality of components is not completely separated. The first time-series data of the fluorescence signal corresponds to N-color-detection time-series data 513 of an M-fluorescent-substance-labeled sample 501, as described below. The computer 520 includes a storage unit (e.g. a memory and a HDD). The storage unit stores in advance second time-series data of individual model fluorescence signals of the plurality of components. The second time-series data of the individual model fluorescence signals of the plurality of components corresponds to N-color-detection time-series data 541 of single peak of each of the M-fluorescent-substance-labeled components described below. The computer 520 compares the first time-series data with the second time-series data, and determines which kind of fluorescent substances of M kinds of fluorescent substances individually label each of the plurality of components. The display device 530 displays third time-series data of concentrations of M kinds of fluorescent substances contributing to the fluorescence signals. The third time-series data of the concentrations of the fluorescent substances corresponds to M-fluorescent-substance-concentration time-series data 523 described below. In the following, the processes will be more specifically described.

First, the M-fluorescent-substance-labeled sample 501 including the plurality of components labeled with M kinds of fluorescent substances is injected into the analyzer 510. Subsequently, in the analyzer 510, a separation analysis process 511 of the plurality of components included in the sample 501 is performed. The analyzer 510 detects fluorescence emissions from M kinds of fluorescent substances in N kinds (M>N) of wavelength bands (N-color detection), and acquires the N-color-detection time-series data (fluorescence detection time-series data) 513 of the M-fluorescent-substance-labeled sample. Here, the plurality of components are not always excellently separated. That is, fluorescence from a part of different components labeled with different fluorescent substances is detected in a space-time overlap state. The analyzer 510 outputs the N-color-detection time-series data 513 to the computer 520.

Subsequently, the computer 520 acquires, as input information, the N-color-detection time-series data 513 and the N-color-detection time-series data 541 of the single peak of each of the M-fluorescent-substance-labeled components. The N-color detection time-series data 541 of the single peak of each of the M-fluorescent-substance-labeled components is data corresponding to FIGS. 3 (5), (6), (7), and (8), for example. Note that the N-color-detection time-series data 541 of the single peak of each of the M-fluorescent-substance-labeled components stored in advance on a first database 540.

Subsequently, the computer 520 executes a comparison analysis process 521 between the N-color-detection time-series data 513 and the N-color-detection time-series data 541 of the single peak of each of the M-fluorescent-substance-labeled components. As a result, the computer 520 acquires the M-fluorescent-substance-concentration time-series data 523 that is the time-series data of the detected concentrations of M kinds of fluorescent substances, i.e., the concentrations of components labeled with M kinds of fluorescent substances. The M-fluorescent-substance-concentration time-series data 523 is data corresponding to FIG. 3 (2), for example. Lastly, the display device 530 performs a display process 531 of the M-fluorescent-substance-concentration time-series data 523.

Figure 6:
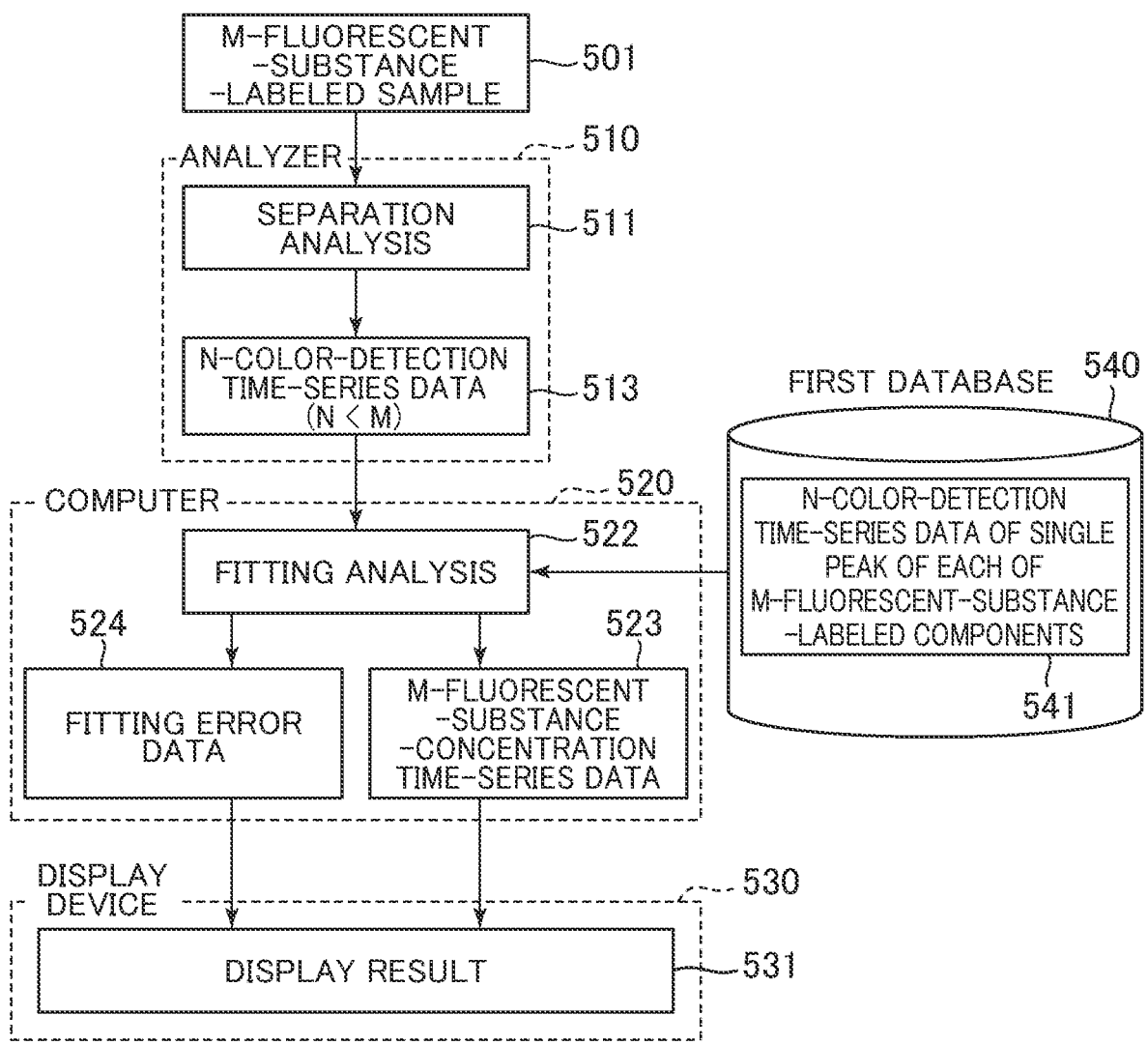
FIG. 6 is a diagram showing process steps and the configuration of a system according to the first embodiment.

FIG. 6 is a diagram that embodies comparison analysis on the computer 520 in FIG. 5. As comparison analysis, the computer 520 performs a fitting analysis process 522 on the N-color-detection time-series data 513 using the N-color-detection time-series data 541 of the single peak of each of the M-fluorescent-substance-labeled components. As a result, the computer 520 acquires fitting error data (or fitting accuracy data) 524 based on difference between the N-color-detection time-series data 513 and its fitting result together with the M-fluorescent-substance-concentration time-series data 523. The display device 530 performs the display process 531 for any of or both of the M-fluorescent-substance-concentration time-series data 523 and the fitting error data 524.

Second Embodiment

Figure 7:
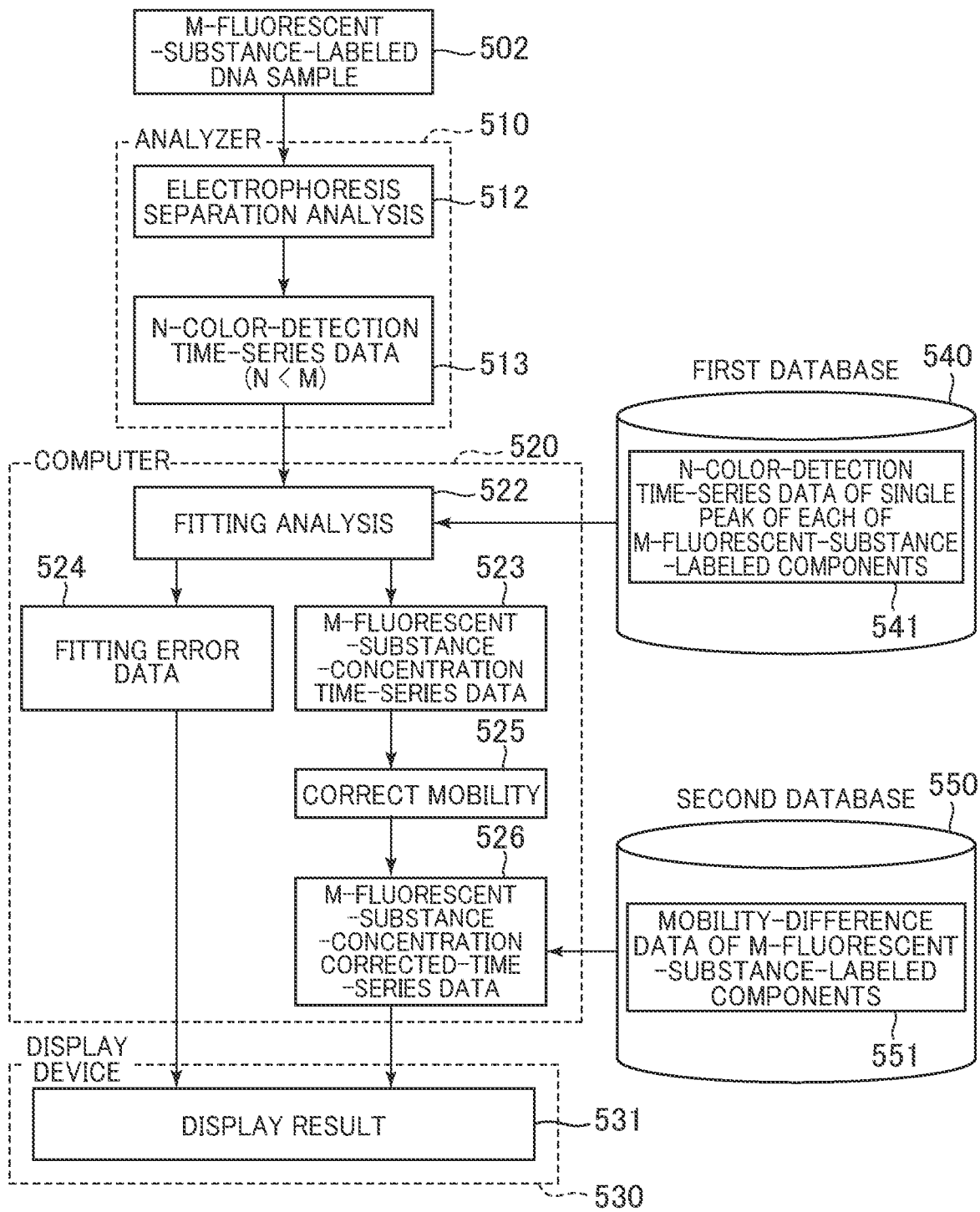
FIG. 7 is a diagram showing process steps and the configuration of a system according to a second embodiment.

FIG. 7 shows the process steps and a configuration of a system in the case in which the present invention is applied to electrophoresis analysis of DNA fragments. A plurality of components that are analytical targets may be nucleic acid fragments of different lengths or different compositions, and chromatography may be electrophoresis.

An analyzer 510 is an electrophoresis apparatus. First, an M-fluorescent-substance-labeled-DNA sample 502 including a plurality of kinds of DNA fragments labeled with M kinds of fluorescent substances is injected into the analyzer 510. Subsequently, in the analyzer 510, an electrophoresis separation analysis process 512 of the plurality of kinds of DNA fragments included in the DNA sample is performed. The analyzer 510 detects the emissions of fluorescence from M kinds of fluorescent substances in N kinds (M>N) of wavelength bands (N-color detection), and acquires N-color-detection time-series data 513. Here, the plurality of kinds of DNA fragments are not always excellently separated. That is, fluorescence from a part of different kinds of DNA fragments labeled with different fluorescent substances is detected in a space-time overlap state. The analyzer 510 outputs the N-color-detection time-series data 513 to a computer 520.

Subsequently, the computer 520 acquires, as input information, the N-color-detection time-series data 513 and N-color-detection time-series data 541 of a single peak of each of M-fluorescent-substance-labeled components that is the N-color-detection time-series data of a single kind of DNA fragments labeled with any one of M kinds of fluorescent substances. Subsequently, the computer 520 performs comparison analysis between the N-color-detection time-series data 513 and the N-color-detection time-series data 541 of the single peak of each of the M-fluorescentsubstance-labeled components. Specifically, the computer 520 performs the fitting analysis process 522 on the N-color-detection time-series data 513 using the N-color-detection time-series data 541 of the single peak of each of the M-fluorescent-substance-labeled components. As a result, the computer 520 acquires M-fluorescent-substance-concentration time-series data 523 that is the time-series data of the detected concentrations of M kinds of fluorescent substances, i.e., the concentration of the DNA fragments labeled with M kinds of fluorescent substances. At the same time, the computer 520 acquires fitting error data (or fitting accuracy data) 524.

Here, the mobility of DNA fragments by electrophoresis is affected by M kinds of fluorescent substances to be labeled. Therefore, in order to reduce the influence, the computer 520 performs a process using mobility-difference data 551 of the M-fluorescent-substance-labeled components indicating the difference in the mobility due to M kinds of fluorescent substances to be labeled. The mobility-difference data 551 of the M-fluorescent-substance-labeled components is stored in advance on a second database 550. The computer 520 executes a mobility correction process 525 on the M-fluorescent-substance-concentration time-series data 523 using the mobility-difference data 551 of the M-fluorescent-substance-labeled components, and acquires M-fluorescent-substance-concentration corrected-time-series data 526 (in the following, referred to as corrected data). The corrected data 526 is data corresponding to FIG. 3 (3), for example.

Lastly, the display device 530 performs a display process 531 for a part or all of the M-fluorescent-substance-concentration time-series data 523, fitting error data (or fitting accuracy data) 524, and the M-fluorescent-substance-concentration corrected-time-series data 526.

Third Embodiment

Figure 8:
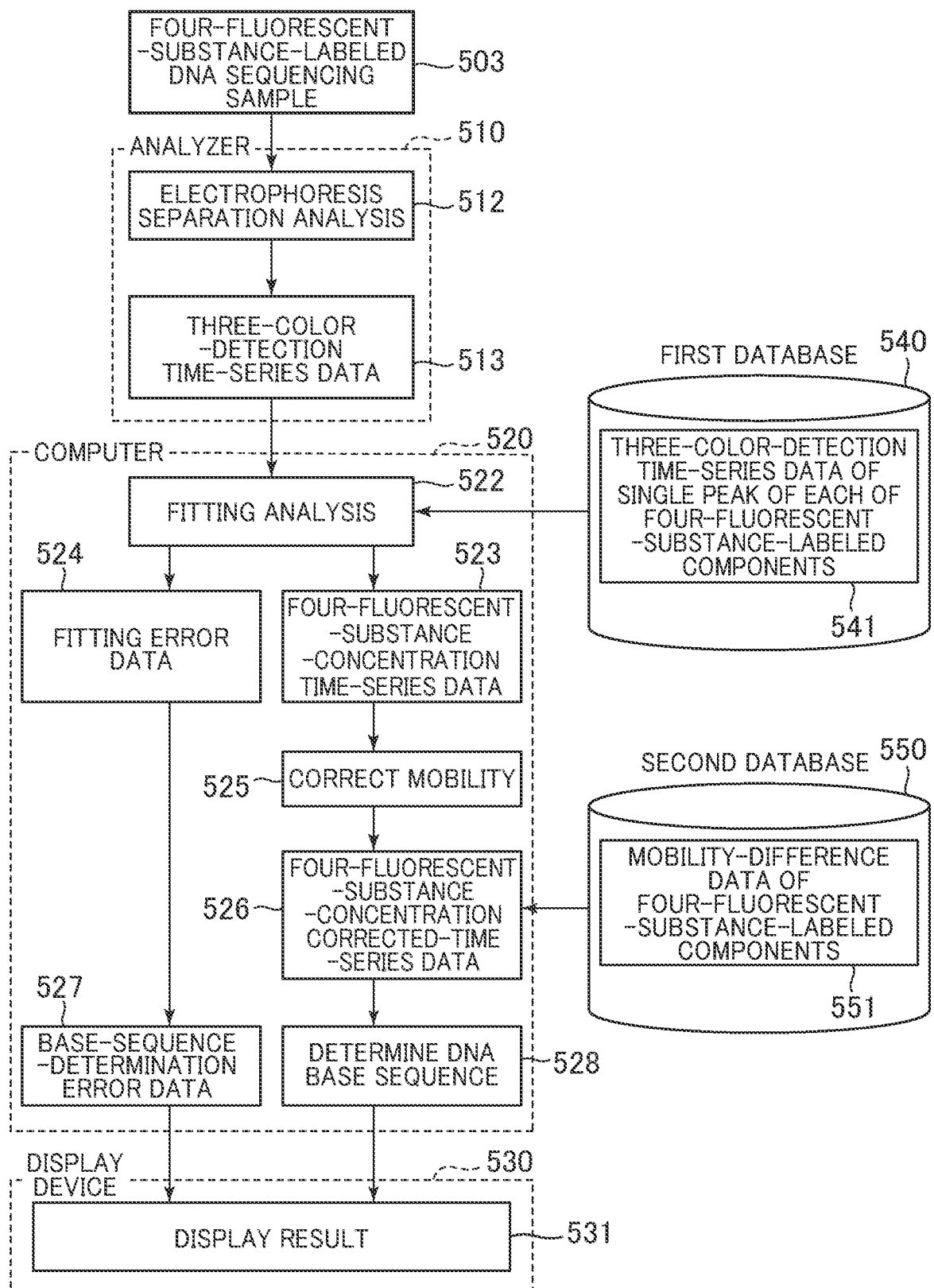
FIG. 8 is a diagram showing process steps and the configuration of a system according to a third embodiment (M=4, N=3).

FIG. 8 shows the process steps and a configuration of a system in the case in which the present invention is applied to DNA sequencing by electrophoresis. In FIG. 8, N=3 and M=4. An analyzer 510 is a DNA sequencer.

First, a four-fluorescent-substance-labeled DNA sequencing sample 503 is prepared. The four-fluorescent-substance-labeled DNA sequencing sample 503 includes four kinds of DNA fragments that are prepared by a Sanger method using a target DNA as a template and labeled with four kinds of fluorescent substances corresponding to four kinds of terminal base species. The four-fluorescent-substance-labeled DNA sequencing sample 503 is injected into the analyzer 510. Subsequently, in the analyzer 510, an electrophoresis separation analysis process 512 is performed on four kinds of DNA fragments included in the DNA sequencing sample. The analyzer 510 detects fluorescence emissions from four kinds of fluorescent substances in three kinds of wavelength bands, and acquires three-color-detection time-series data 513. Here, four kinds of DNA fragments are not always excellently separated. That is, fluorescence from a part of the DNA fragments of different lengths labeled with different fluorescent substances is detected in the space-time overlap state. The analyzer 510 outputs the three-color-detection time-series data 513 to a computer 520.

Subsequently, the computer 520 acquires, as input information, the three-color detection time-series data 513 and three-color-detection time-series data 541 of a single peak of each of four-fluorescent-substance-labeled components that is the three-color-detection time-series data of the DNA fragments of a single length labeled with any one of four kinds of fluorescent substances. The three-color-detection time-series data 541 of the single peak of each of the four-fluorescent-substance-labeled components is stored in advance on a first database 540. The computer 520 performs comparison analysis between the three-color-detection time-series data 513 and the three-color-detection time-series data 541 of the single peak of each of the four-fluorescent-substance-labeled components. Specifically, the computer 520 performs a fitting analysis process 522 on the three-color-detection time-series data 513 of the four-fluorescent-substance-labeled DNA sequencing sample using the three-color-detection time-series data 541 of the single peak of each of the four-fluorescent-substance-labeled components. As a result, the computer 520 acquires four-fluorescent-substance-concentration time-series data 523 that is the time-series data of the detected concentrations of four kinds of fluorescent substances, i.e., the concentrations of four kinds of DNA fragments having different terminal base species and labeled with four kinds of fluorescent substances. At the same time, the computer 520 acquires fitting error data (or fitting accuracy data) 524.

Here, the mobility of DNA fragments by electrophoresis is affected by four kinds of fluorescent substances to be labeled. Therefore, in order to reduce the influence, a process is performed using mobility-difference data 551 of four-fluorescent-substance-labeled components indicating the difference in the mobility due to four kinds of fluorescent substances to be labeled. The mobility-difference data 551 of four-fluorescent-substance-labeled components is stored in advance on a second database 550. The computer 520 executes a mobility correction process 525 on the four-fluorescent-substance-concentration time-series data 523 using the mobility-difference data 551 of four-fluorescent-substance-labeled components, and acquires four-fluorescent-substance-concentration corrected-time-series corrected data (in the following, referred to as corrected data) 526.

The computer 520 performs a DNA base sequence determination process 528 using the four-fluorescent-substance-concentration corrected-time-series data 526. On the other hand, the computer 520 acquires base-sequence-determination error data (or base-sequence-determination accuracy data) 527 of each base of the determined DNA base sequence using the fitting error data (or fitting accuracy data) 524.

Lastly, the display device 530 performs a display process 531 for a part or all of the four-fluorescent-substance-concentration time-series data 523, the fitting error data (or fitting accuracy data) 524, the four-fluorescent-substance-concentration corrected-time-series data 526, the DNA-base-sequence-determination results, and the base-sequence-determination error data (or base-sequence-determination accuracy data) 527.

Fourth Embodiment

Figure 9:
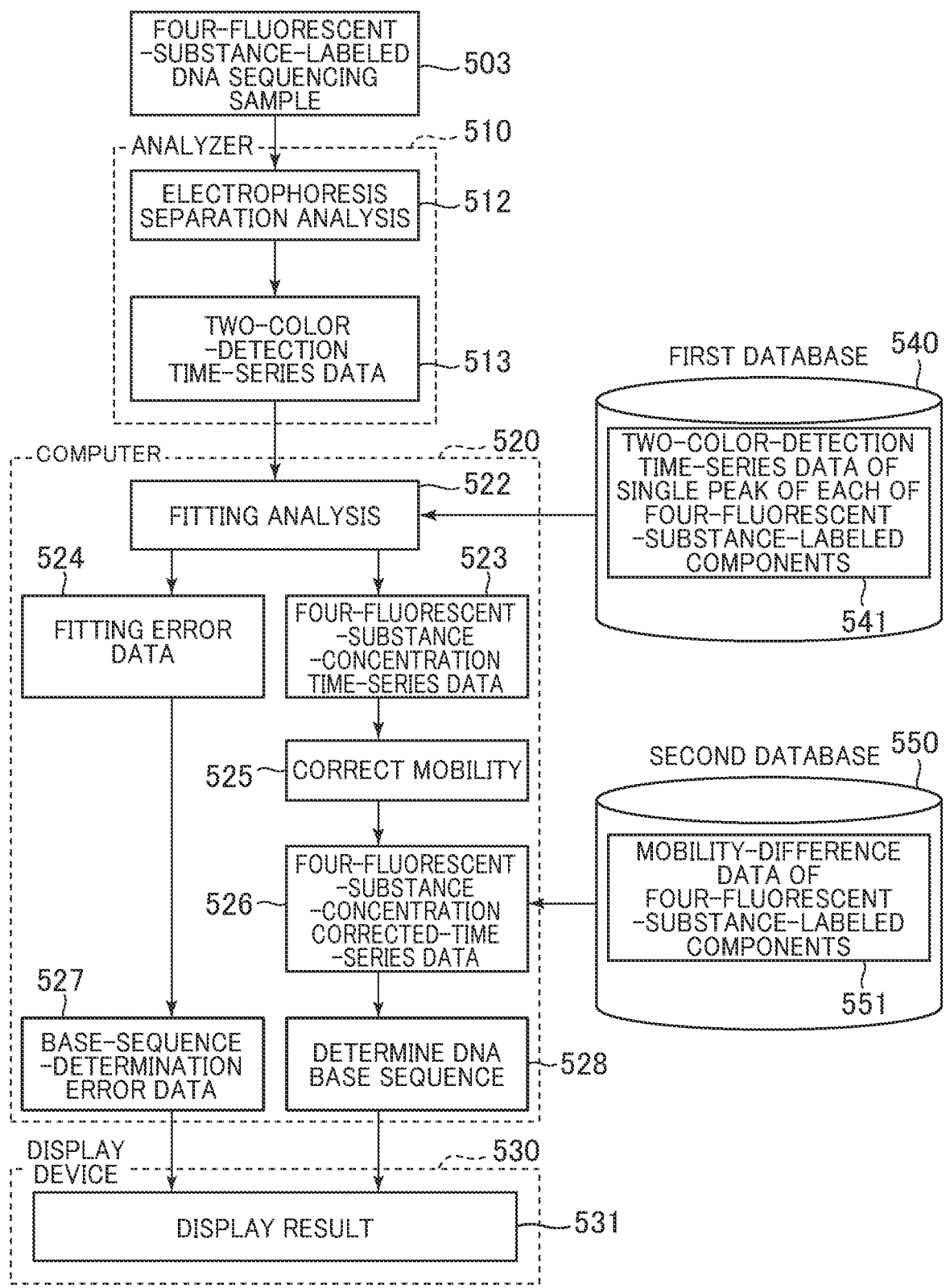
FIG. 9 is a diagram showing process steps and the configuration of a system according to a fourth embodiment (M=4, N=2).

FIG. 9 shows the process steps and a configuration of a system in the case in which the configuration of FIG. 8 is substituted under the conditions N=2 and M=4. The process steps and the configuration of the system are similar to FIG. 8, and the description is therefore omitted.

Figure 10:
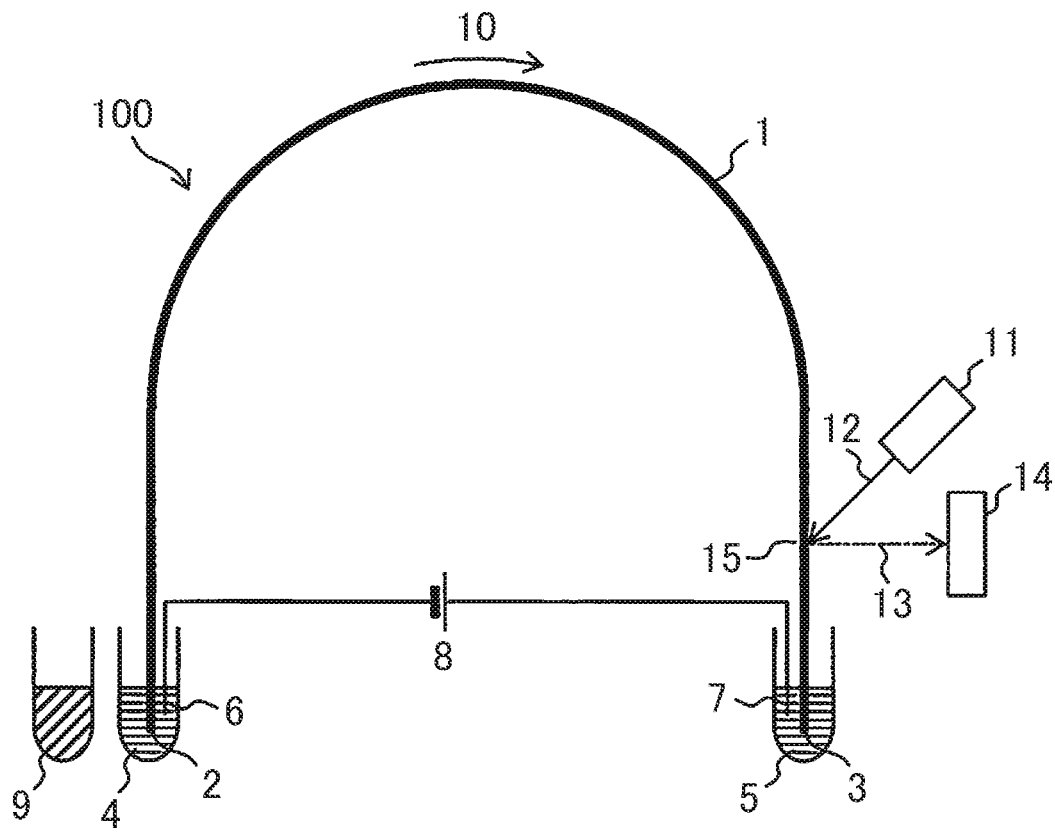
FIG. 10 is a block diagram of a multi-capillary-electrophoresis apparatus.

FIG. 10 is a block diagram of a multi-capillary electrophoresis apparatus that is an example of the analyzer 510. A capillary electrophoresis apparatus 100 is used as a DNA sequencer and a DNA fragment analysis device, for example. The inside of a capillary 1 is filled with an electrophoresis separation medium having electrolyte, and a sample injection end 2 and a sample elution end 3 of the capillary 1 are respectively immersed in a cathode-side electrolytic solution 4 and an anode-side electrolytic solution 5, respectively. A negative electrode 6 is immersed in the cathode-side electrolytic solution 4, and a positive electrode 7 is immersed in the anode-side electrolytic solution 5. A high-voltage power supply 8 applies a high voltage across the negative electrode 6 and the positive electrode 7, and hence electrophoresis is performed.

The sample injection to the capillary 1 is performed in which the sample injection end 2 and the negative electrode 6 are immersed in a sample solution 9 and the high-voltage power supply 8 applies a high voltage across the negative electrode 6 and the positive electrode 7 for a short time. The sample solution 9 includes a plurality of kinds of components labeled with a plurality of kinds of fluorescent substances. After sample injection, the sample injection end 2 and the negative electrode 6 are again immersed in the cathode-side electrolytic solution 4, a high voltage is applied across the negative electrode 6 and the positive electrode 7, and hence electrophoresis is performed.

Negatively charged components included in the sample solution 9, e.g. DNA fragments are electrophoretically migrated in an electrophoresis direction 10, indicated by an arrow, from the sample injection end 2 to the sample elution end 3 in the capillary 1. By the difference in the mobility due to electrophoresis, the plurality of kinds of components included in the sample solution 9 is gradually separated. At a position (a laser beam irradiation position 15) where the components electrophoretically migrated by a certain distance in the capillary 1, a laser beam 12 emitted from a laser light source 11 is irradiated. When the components pass the laser beam irradiation position 15, emission of fluorescence 13 from the plurality of kinds of fluorescent substances labeled on the components is induced. The fluorescence 13 varying over time of electrophoresis is measured by a multicolor detection system 14 that performs optical detection in a plurality of kinds of wavelength bands. Although only one capillary 1 is depicted in FIG. 10, there may be used a multi-capillary electrophoresis apparatus that performs electrophoresis analysis in parallel using a plurality of capillaries 1.

Figure 11:
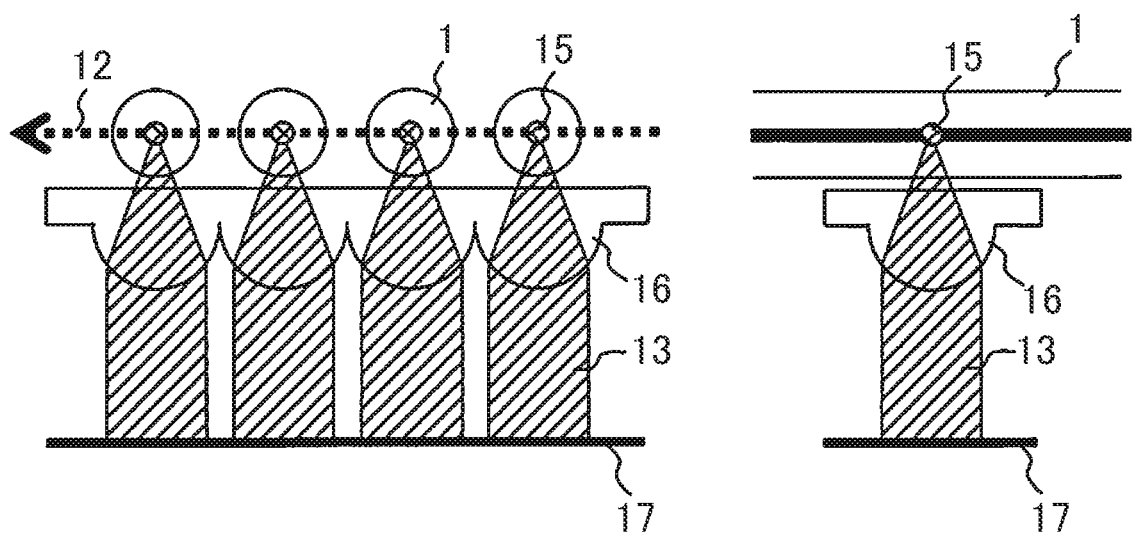
FIG. 11 is a block diagram of a multicolor detection system of the multi-capillary-electrophoresis apparatus.

FIG. 11 shows an example of a multicolor detection system of a multi-capillary electrophoresis apparatus. The laser beam irradiation positions 15 of a plurality of capillaries 1 are arranged on the same plane at regular intervals. The left drawing in FIG. 11 is a cross-sectional view vertical to the major axis of the plurality of capillaries 1, and the right drawing in FIG. 11 is a cross-sectional view parallel with the major axis of a given capillary 1.

The laser beam 12 is irradiated along the arrangement plane of the plurality of capillaries 1. Thus, the laser beam 12 is simultaneously irradiated to the plurality of capillaries 1. The fluorescence 13 emitted from each of the capillaries 1 is condensed in parallel by separate lenses 16. The condensed beams directly enter a two-dimensional color sensor 17. The two-dimensional color sensor 17 is an RGB color sensor that can perform three-color detection in three kinds of wavelength bands. The fluorescence 13 emitted from the capillaries 1 respectively forms spots at different positions on the two-dimensional color sensor 17, and hence the fluorescence 13 can be independently detected in three colors.

Figure 12:
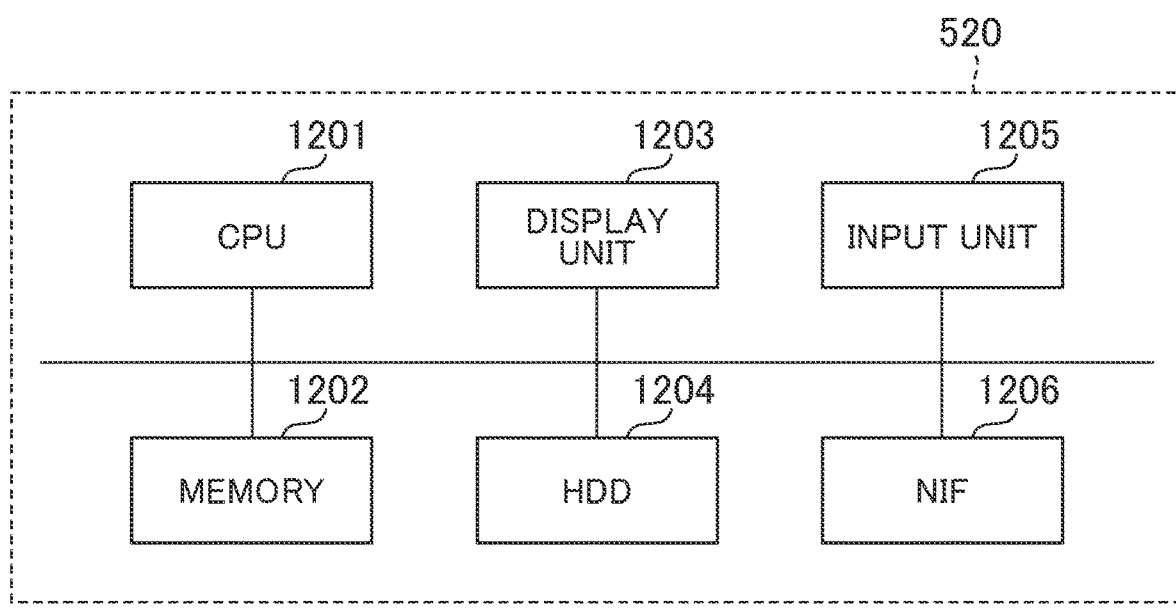
FIG. 12 is a block diagram of a computer.

FIG. 12 shows an exemplary configuration of a computer 520. As shown in FIGS. 5 to 9, the computer 520 is connected to the analyzer 510. The computer 520 may control not only data analysis described in FIGS. 5 to 9 but also the analyzer 510. In FIGS. 5 to 9, a display device 530 and databases 540 and 550 are depicted on the outer side of the computer 520. However, the databases 540 and 550 may be included in the computer 520.

The computer 520 includes a CPU (processor) 1201, a memory 1202, a display unit 1203, a HDD 1204, an input unit 1205, and a network interface (NIF) 1206. The display unit 1203 is a display, for example, and may be used as the display device 530. The input unit 1205 is an input device that is a keyboard and a mouse, for example. A user can set the conditions of data analysis and the conditions of controlling the analyzer 510 through the input unit 1205. N-color detection time-series data 513 outputted from the analyzer 510 is sequentially stored on the memory 1202.

The HDD 1204 may include the databases 540 and 550. The HDD 1204 may include programs that perform the fitting analysis process, the mobility correction process, and the DNA base sequence determination process, and any other process of the computer 520. The process of the computer 520 may be achieved in which processes corresponding to program codes are stored on the memory 1202 and the CPU 1201 executes the program codes.

For example, N-color-detection time-series data 541 of the single peak of each of the M-fluorescent-substance-labeled components—stored on the HDD 1204 is stored on the memory 1202, and the CPU 1201 executes the comparison analysis process using the N-color-detection time-series data 513 and the N-color-detection time-series data 541 of the single peak of each of the M-fluorescent-substance-labeled components-. The display unit 1203 displays the analyzed results. Note that the analyzed results may be checked against information on a network through the NIF 1206.

Fifth Embodiment

FIGS. 13 to 18 show an embodiment in which DNA sequencing is performed using the process steps and the configurations of the system shown in FIGS. 9 to 12.

As a four-fluorescent-substance-labeled DNA sequencing sample, a sample was prepared by dissolving 3500/3500×L Sequencing Standards, BigDye Terminator v3.1 (Thermo Fisher Scientific) in 300 μL of formamide. This sample includes four kinds of DNA fragments having terminal base species C, A, G, and T labeled with four kinds of fluorescent substances dROX (a maximum emission wavelength of 618 nm), dR6G (a maximum emission wavelength of 568 nm), dR110 (541 nm), and dTAMRA (a maximum emission wavelength of 595 nm), respectively.

There are four capillaries 1 with an outer diameter of 360 μm, an inner diameter of 50 μm, a total length of 56 cm, and an effective length of 36 cm. For the electrophoresis separation medium, POP-7 (Thermo Fisher Scientific) that is a polymer solution was used. In electrophoresis, the capillary 1 was adjusted to a temperature of 60° C., and the electric field strength was 182 V/cm. The sample injection was performed by electrokinetic injection at an electric field strength of 27 V/cm for eight seconds. The laser beam 12 was at a wavelength of 505 nm and an output of 20 mW. Between the lens 16 and the two-dimensional color sensor, a long-pass filter that blocked the laser beam 12 was used.

Figure 13:
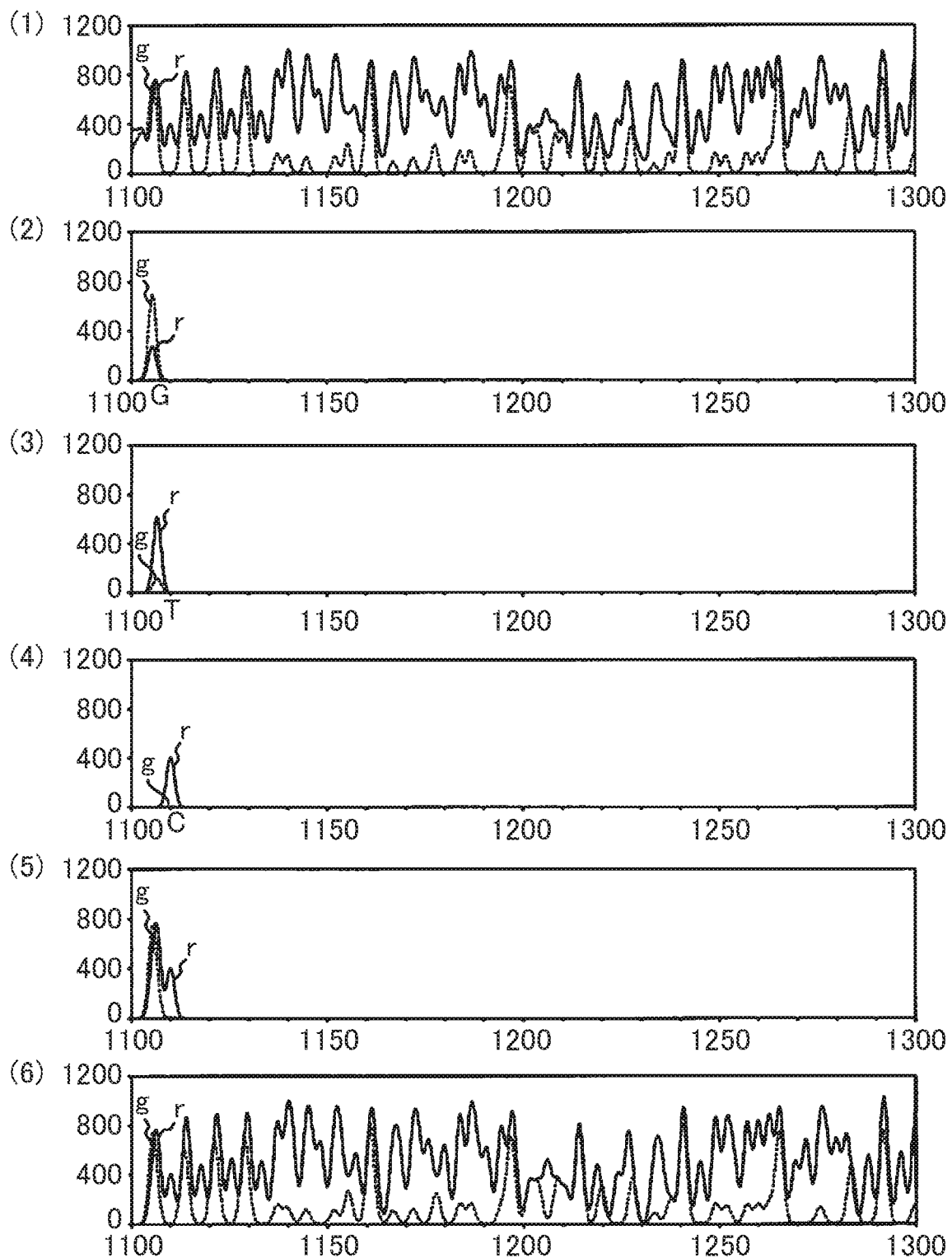
FIG. 13 shows a fifth embodiment in which DNA sequencing is performed using the process steps and the configurations of the system shown in FIGS. 9 to 12.

FIG. 13 (1) corresponds to FIG. 4 (1), and is two-color-detection time-series data obtained by detecting fluorescence 13 emitted one of four capillaries 1 by the RGB color sensor during electrophoresis. The RGB color sensor used in the embodiment can perform three-color detection with three kinds of wavelength bands r, g, and b corresponding to R (red), G (green), and B (blue). However, the emissions of fluorescence from four kinds of fluorescent substances were rarely detected in the wavelength band b, and were detected only in the wavelength bands r and g. Thus, FIG. 13 (1) shows a time series of the fluorescence intensity I(r) and I(g) in these two colors. The horizontal axis expresses a lapse of time (electrophoresis time) from the start of electrophoresis in units of seconds, and the vertical axis expresses the fluorescence intensity in arbitrary unit.

Figure 14:
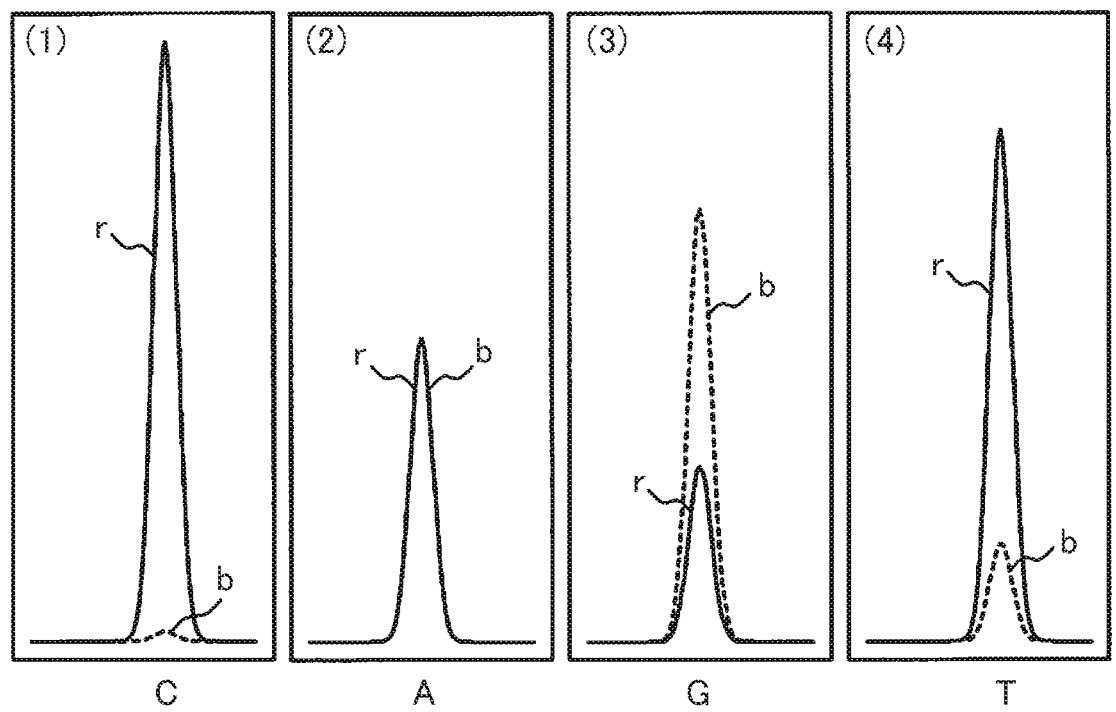
FIG. 14 is a diagram showing time-series data of two color fluorescence intensities of model peaks of certain-length DNA fragments labeled with four kinds of fluorescent substances according to the fifth embodiment.

FIG. 14 (1) corresponds to FIG. 4 (5), and is time-series data of two color fluorescence intensities I(g) and I(r) of a model peak when DNA fragments having terminal base species C and a certain length, and labeled with the fluorescent substance dROX were detected in two colors. Here, ratio of the two color fluorescence intensities at any time is $(w(gC)\ w(rC))^T=(0.02\ 0.98)^T$. Similarly, FIG. 14 (2) corresponds to FIG. 4 (6), and is time-series data of two color fluorescence intensities I(g) and I(r) of a model peak when DNA fragments having terminal base species A and a certain length, and labeled with the fluorescent substance dR6G were detected in two colors. Ratio of the two color fluorescence intensities is $(w(gA)\ w(rA))^T=(0.50\ 0.50)^T$. FIG. 14 (3) corresponds to FIG. 4 (7), and is time-series data of two color fluorescence intensities I(g) and I(r) of a model peak when DNA fragments having terminal base species G and a certain length, and labeled with the fluorescent substance dR110 were detected in two colors. Ratio of the two color fluorescence intensities is $(w(gG)\ w(rG))^T=(0.71\ 0.29)^T$. FIG. 14 (4) corresponds to FIG. 4 (8), and is time-series data of two color fluorescence intensities I(g) and I(r) of a model peak when DNA fragments having terminal base species T and a certain length, and labeled with the fluorescent substance dTAMRA were detected in two colors. Ratio of the two color fluorescence intensities is $(w(gT)\ w(rT))^T=(0.16\ 0.84)^T$. Shapes, offsets, and standard deviation of the model peaks were Gaussian, zero, and one second, respectively. These values matched with those experimentally measured under the present electrophoresis conditions.

The two-color-detection time-series data of four kinds of model peaks shown in FIGS. 14 (1) to (4) were sequentially fit to the two-color-detection time-series data obtained by electrophoresis analysis shown in FIG. 13 (1). In the fitting, only medians (electrophoresis times) and heights (fluorescence intensities) of the Gaussian distributions shown in FIGS. 14 (1) to (4) were varied while the two color fluorescence intensity ratios and standard deviations of the Gaussian distributions were kept, and the medians and the heights were determined such that the errors from the two-color-detection time-series data in FIG. 13 (1) were minimized.

FIG. 13 (2) is the result that the model peak of G (dR110) in FIG. 14 (3) was accurately fit to the peak of g observed on the leftmost of FIG. 13 (1). FIG. 13 (3) is the result that the model peak of T (dTAMRA) in FIG. 14 (4) was accurately fit to the peak of r on the right side of the above peak of g in FIG. 13 (1). FIG. 13 (4) is the result that the model peak of C (dROX) in FIG. 14 (1) was accurately fit to the peak of r on the right side of the above peak of r in FIG. 13 (1). FIG. 13 (5) is the two-color-detection time-series data that summated those in FIGS. 13 (2), (3) and (4), i.e., time-series data that added I(g) and I(r) in FIGS. 13 (2), (3) and (4). As shown in FIG. 13 (5), two-color-detection time-series data faithfully fitted to the corresponding portions of the two-color-detection time-series data in FIG. 13 (1) were reproduced.

Fitting error and fitting accuracy were evaluated as below. Fitting error was found by dividing standard deviation of difference between a fit model peak and the corresponding measured two-color-detection time-series data in a section of two-second duration (two times the standard deviation of the Gaussian distribution) center of which is the time of the top of the fit model peak, by a larger value of the measured two-color-fluorescence intensities at the time of the top of the fit model peak. Fitting accuracy was obtained by subtracting the corresponding fitting error from one. Fitting accuracy is 100% when a fit model peak perfectly agrees with the corresponding measured two-color-detection time-series data. Then fitting accuracy decreases with deviation between the fit model peak and the measured two-color-detection time-series data, and becomes 0% when the deviation is larger than or equal to the larger value of the measured two-color-fluorescence intensities. In the embodiment, fitting error and accuracy are defined as described above. However, definitions other than these are of course fine.

The fitting accuracy of the fit model peak of T in FIG. 13 (3) alone was only 43.41%. However, the fitting accuracy of the fit model peak of T when the fit model peaks of G, T, and C were summated as shown in FIG. 13 (5) was 95.56%. This means that in the case in which the space-time overlap is present, it is important to perform fitting neighboring model peaks together rather than a model peak alone.

Similarly, the two-color-detection time-series data of four kinds of model peaks shown in FIGS. 14 (1) to (4) were sequentially fit to all the peaks of g and r in FIG. 13 (1). As shown in FIG. 13 (6), two-color-detection time-series data faithfully fitted to the two-color-detection time-series data in FIG. 13 (1) were reproduced by summating all the fit model peaks.

Figure 15:
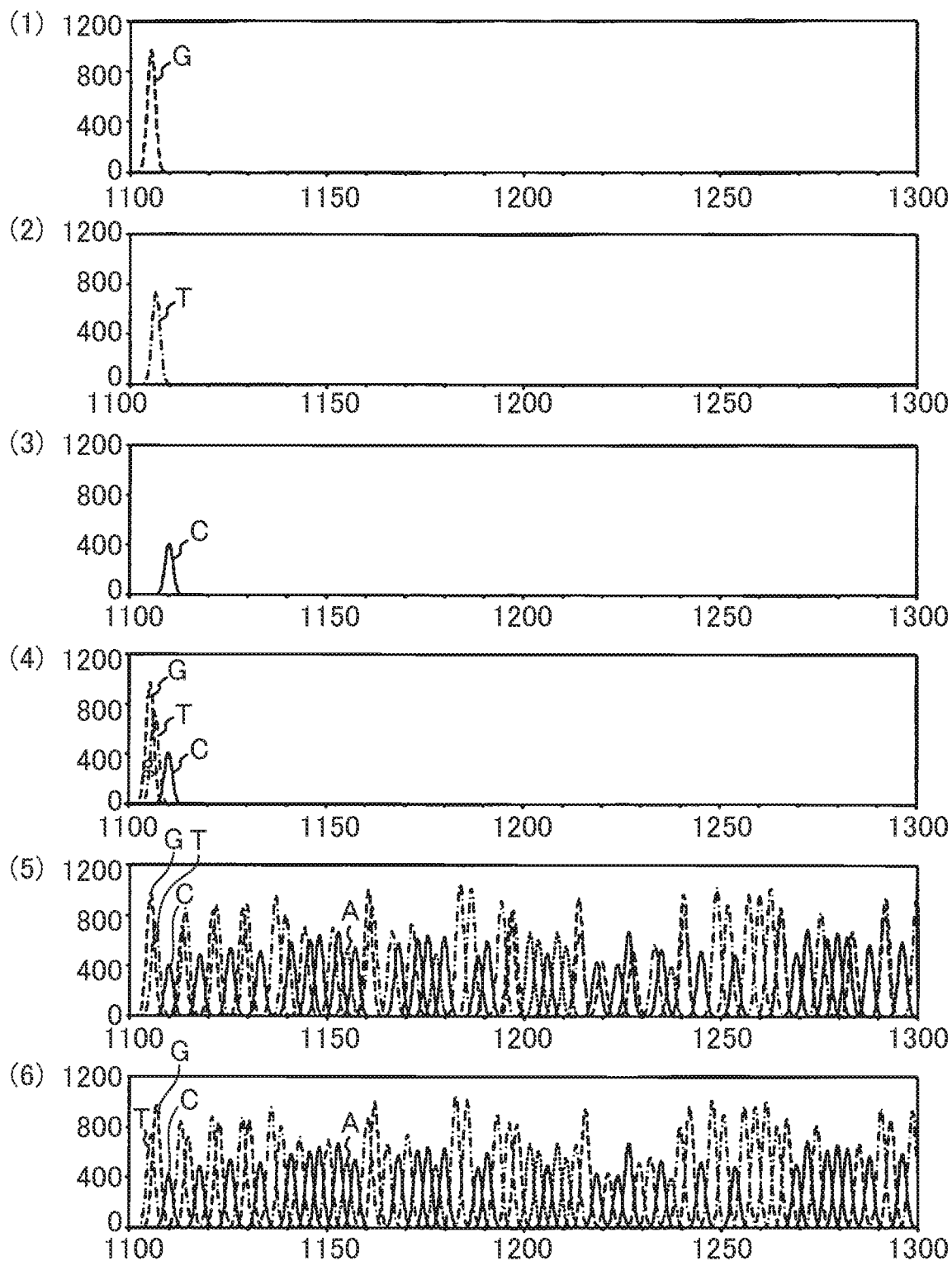
FIG. 15 is a diagram illustrating the process of DNA sequencing according to the fifth embodiment.

FIG. 15 (1) shows time-series data of concentration of the fluorescent substance dR110, i.e., concentration of DNA fragments of the terminal base species G, obtained by summating I(g) and I(r) in FIG. 13 (2). FIG. 15 (2) shows time-series data of concentration of the fluorescent substance dTAMRA, i.e., concentration of DNA fragments of the terminal base species T, obtained by summating I(g) and I(r) in FIG. 13 (3). FIG. 15 (3) shows time-series data of concentration of the fluorescent substance dROX, i.e., concentration of DNA fragments of the terminal base species C obtained by summating I(g) and I(r) in FIG. 13 (4). Similarly, FIG. 15 (5) shows time-series data of concentrations of DNA fragments of the terminal base species C, A, G, and T obtained by all the fit model peaks in FIG. 13 (6).

FIG. 17 shows a list summarizing terminal base species, fitting accuracy, and QV (Quality Value) on all the fit model peaks in FIG. 15 (5) in the temporal order of electrophoresis. Here, QV is found from QV=−10*Log (1−S) where the fitting accuracy is S. In 200 seconds from electrophoresis time 1100 seconds to 1300 seconds, 76 kinds of DNA fragments of different base lengths are measured, and their terminal base species are individually identified. Because the fitting accuracy is a mean of 94.72%, and the QV is a mean of 13.95, highly accurate fitting is achieved. Note that the computer 520 may calculate data in FIG. 17, and the display device 530 may display data in FIG. 17.

FIG. 15 (6) shows corrected time-series data of concentrations of the DNA fragments of the terminal base species C, A, G, and T obtained by applying mobility correction to FIG. 15 (5) based on the difference in mobility due to the differences between four kinds of fluorescent substances. Specifically, electrophoresis times of the medians of the fit model peaks of the terminal base species G in FIG. 15 (5) was shifted backward by 1.6 seconds, electrophoresis times of the medians of the fit model peaks of the terminal base species T in FIG. 15 (5) was shifted forward by 1.1 seconds, and the fit model peaks of the terminal base species C and A were not corrected. As a result above, the peaks of the DNA fragments of different base lengths were arranged almost at regular intervals. Notably, measurement order of the DNA fragments of the terminal base species G and the terminal base species T are reversed because of the influence of the difference in mobility (that is, long DNA fragments overtakes short DNA fragments in electrophoresis) as shown in FIG. 15 (5), whereas it is excellently corrected as shown in FIG. 15(6).

FIG. 18 shows a list summarizing terminal base species, fitting accuracy, and QV on all the fit model peaks in FIG. 15 (6) in the corrected temporal order of electrophoresis. FIG. 18 is the list that rearranges FIG. 17, and the numerical values used are the same. The arrangement of the terminal base species in FIG. 18 provides DNA sequencing results (base-calling results). Fitting accuracy and QV of the bases are indexes in correlation with base-calling accuracy, but are not the same with base-calling accuracy. Generally, it is expected that base-calling accuracy of is greater than fitting accuracy. Actually, accuracy of the DNA sequencing results in FIG. 18 was 100%. Note that the computer 520 may calculate the data in FIG. 18, and the display device 530 may display the data in FIG. 18.

Figure 16:
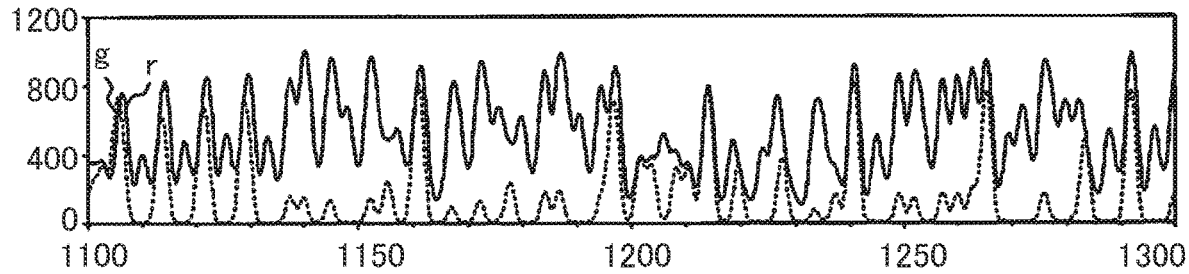
FIG. 16 is a diagram illustrating the process of DNA sequencing according to the fifth embodiment.
Figure 16:
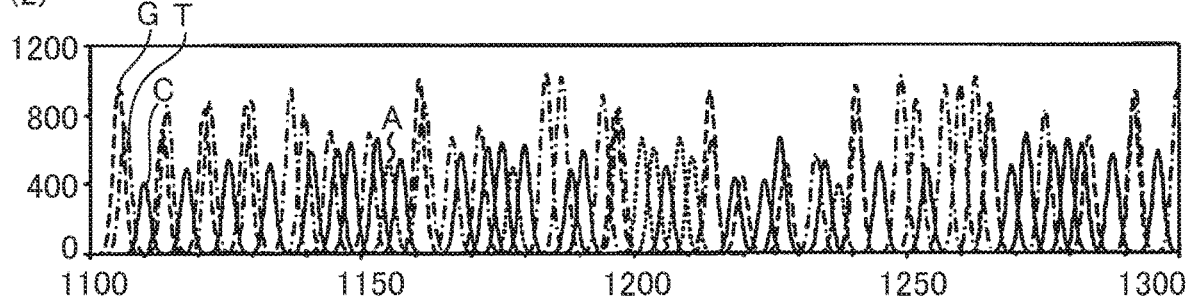
Figure 16:
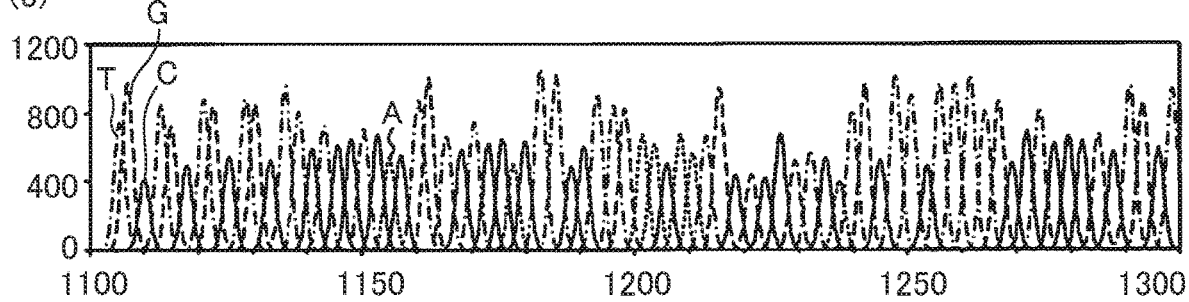
Figure 16:
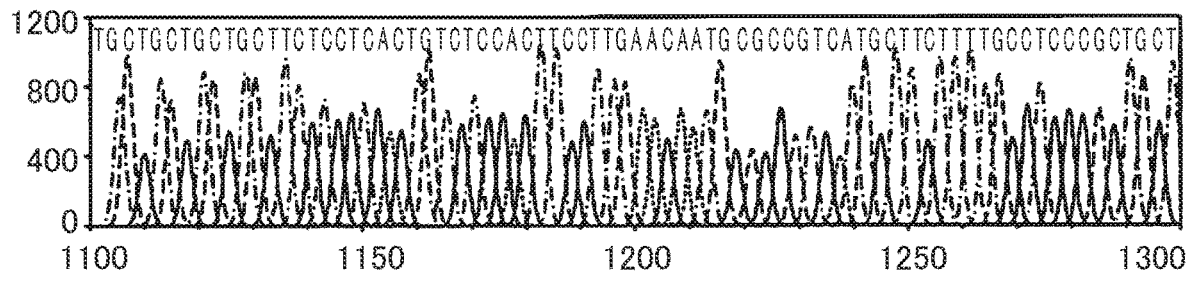

FIG. 16 summarizes the processes of DNA sequencing according to the embodiment. FIG. 16 (1) is the same as FIG. 13 (1), and is the two-color-detection time-series data obtained by electrophoresis analysis, corresponding to FIG. 4 (1). FIG. 16 (2) is the same as FIG. 15 (5), and is the time-series data of concentrations of the DNA fragments of the terminal base species C, A, G, and T, corresponding to FIG. 4 (2). FIG. 16 (3) is the same as FIG. 15 (6), and is the corrected-time-series data of concentrations of the DNA fragments of the terminal base species C, A, G, and T obtained by mobility correction in FIG. 16 (2), corresponding to FIG. 4 (3). Lastly, FIG. 16 (4) shows the results of performing base-calling based on the results in FIG. 16 (3), corresponding to FIG. 4 (4). The base-calling results in FIG. 16 (4) are matched with the base sequences of the target DNA.

The schemes and the effects of the first to the fifth embodiments will be summarized. According to the foregoing embodiments, analysis methods can be provided in which M kinds of components are identified and detected by N-color detection in N kinds (M>N) of wavelength bands in the state in which fluorescence emitted from M kinds of fluorescent substances has spectral overlaps and space-time overlaps. In the following, following Nonpatent Literature 2, on a DNA sequencer using electrophoresis, a scheme that detects emissions of fluorescence from M=four kinds of fluorescent substances in N=three colors will be described.

The analyzer 510 detects the emissions of fluorescence from four kinds of fluorescent substances C, A, G, and T in three colors in three kinds of wavelength bands b, g, and r. The process is similar to Nonpatent Literature 2 up to the process of obtaining the three-color-fluorescence intensities in Equation (3) at each time. Here, the HDD (the storage unit) 1204 of the computer 520 stores model peak data, that is, time-series data of three color fluorescence intensities of model peaks when DNA fragments of certain lengths labeled with any of four kinds of fluorescent substances, C, A, G, and T are detected in three colors. The three-color-fluorescence intensity ratio of the model peaks of the DNA fragments labeled with the fluorescent substance Y (C, A, G, or T) is $(w(bY)\ w(gY)\ w(rY))^T)^T$. Therefore, the model peak data includes information equivalent to the matrix W. In addition to this, the model peak data includes information on the shapes of the model peaks, i.e., time-series information.

In Nonpatent Literature 2, one kind or two kinds of fluorescent substances emitting fluorescence are selected at each time, and their concentrations are found using the matrix W. On the other hand, in the foregoing embodiments, the computer 520 executes the fitting analysis process to the time-series data of the three-color-fluorescence intensities expressed by Equation (3) using the model peak data of four kinds of fluorescent substances. Even in the case in which fluorescence emitted from four kinds of fluorescent substances has a spectral overlap and a space-time overlap, the computer 520 can execute the fitting analysis process. For example, there is no problem when three kinds or more fluorescent substances emit fluorescence at a time. The fitting results composed of the model peak data of C, A, G, and T expresses the time-series data of concentrations D(C), D(A), D(G), and D(T) of C, A, G, and T. That is, although not color conversion is performed, the concentrations of four kinds of fluorescent substances, i.e., the time-series data of the concentration of four base species corresponding to Equation (2) of Nonpatent Literature 1 can be acquired using the time-series data of the three color fluorescence intensities. Unlike Nonpatent Literature 2, the foregoing embodiments have significant characteristics that utilize time-series information on the concentrations of four kinds of fluorescent substances. After that, the computer 520 performs processes equivalent to the processes (3) and (4) in Nonpatent Literature 1, and hence the computer 520 can acquire the results of base-calling.

According to the foregoing embodiments, fitting is performed to the time-series data of N-color-fluorescence intensities obtained in N kinds (M>N) of wavelength bands by N-color detection in the state in which fluorescence emitted from M kinds of fluorescent substances has spectral overlaps and space-time overlaps using the model peak data of M kinds of fluorescent substances, and hence the time-series data of the concentrations of M kinds of fluorescent substances, i.e., M kinds of components can be analyzed.

In order to perform analysis in which M kinds of components are identified and detected by N-color detection in N kinds of wavelength bands in the state in which fluorescence emitted from M kinds of fluorescent substances has a spectral overlap and a space-time overlap, conventionally, the necessary conditions are M≤N. According to the foregoing embodiments, analysis can be similarly performed in which M kinds of components are identified and detected even in M>N. That is, the effect is exerted in which similar analysis can be achieved by much simpler, smaller-sized, and inexpensive device configuration. For example, by N=three-color detection using an RGB color sensor which performance is being enhanced and which cost is being reduced rapidly, analysis in which M=four kinds or more components labeled with M=four kinds or more fluorescent substances are identified and detected is feasible. From the results above, analysis by highly accurate and inexpensive multicolor detection is feasible. For example, N=three-color detection using an inexpensive RGB color sensor is performed while M=four kinds of DNA fragments labeled with M=four kinds of fluorescent substances by the Sanger reaction, being subjected to electrophoresis separation. Thus, even though the DNA fragments of different lengths labeled with M=four kinds of fluorescent substances are measured in the mixed state, the time-series data of the concentrations of M=four kinds of DNA fragments can be acquired, and hence DNA sequencing can be excellently performed.

The present invention is non-limiting to the foregoing embodiments, including various exemplary modifications. The foregoing embodiments are described in detail for easily understanding the present invention, and are not necessarily limited to those having all the configurations. A part of the configuration of an embodiment may be substituted for the configuration of another embodiment. To the configuration of an embodiment, the configuration of another embodiment may be added. The other configurations can be added to, removed from, or replaced by a part of the configuration of the embodiments.

The configurations, functions, processing units, and processing schemes, for example, of the computer 520 may be achieved by hardware by designing a part or all of those using an integrated circuit, for example. The configurations, functions, and any other component may be achieved by software by a processor that interprets and executes programs implementing the functions. Information, such as programs, tables, and files, that achieves the functions can be stored on various types of computer readable media. Examples of the non-transitory computer readable media that are used include a flexible disk, CD-ROM, DVD-ROM, hard disk, optical disk, magneto-optical disk, CD-R, magnetic tape, non-volatile memory card, and ROM.

In the foregoing embodiments, control lines and information lines that are considered as necessary lines for description are shown. All control lines and information lines of products are not necessarily shown. All the configurations may be connected to each other.

LIST OF REFERENCE SIGNS c Fluorescence signal detected in wavelength band c
g Fluorescence signal detected in wavelength band g
y Fluorescence signal detected in wavelength band y
r Fluorescence signal detected in wavelength band r
C Fluorescent substance C or base species C
A Fluorescent substance A or base species A
G Fluorescent substance G or base species G
T Fluorescent substance T or base species T
1 Capillary
2 Sample injection end
3 Sample elution end
4 Cathode-side electrolytic solution
5 Anode-side electrolytic Solution
6 Negative electrode
7 Positive electrode
8 High-voltage power supply
9 Sample solution
10 Electrophoresis direction
11 Laser light source
12 Laser beam
13 Fluorescence
14 Multicolor detection system
15 Laser beam irradiation position
16 Lens
17 Two-dimensional color sensor
510 Analyzer
520 Computer
530 Display device
540, 550 Database

The invention claimed is:

1. An analysis system comprising:
an analyzer configured to separate a sample including a plurality of components by chromatography, wherein the plurality of components comprise M kinds of components each of which is labeled with a different fluorescent substance, wherein the M is an integer greater than 1, and acquire first time-series data of fluorescence signals detected in N kinds of wavelength bands for each of the different fluorescent substances, wherein N is an integer greater than 1 and M is greater than the N, in a state in which at least a portion of the plurality of components is not completely separated;
a storage device configured to store second time-series data of individual model fluorescence signals of each of the M kinds of components each of which is labeled with the different fluorescent substance detected in the N kinds of wavelength bands, each second time-series data of the individual model fluorescence signals of each of the M kinds of components indicates a temporal change in fluorescence intensity in the N kinds of wavelength bands;
a processor coupled to the storage device; and
a memory coupled to the processor storing instructions, that when executed by the processor, configure the processor to:
store the acquired first time-series data having the detected fluorescence signals, the detected fluorescence signals including detected fluorescence signals of two or more of the M kinds of components in a space-time overlap,
perform fitting of peaks of the first time-series data with peaks of the second time-series data of each of the individual model fluorescence signals of each of the M kinds of components, and
determine which of the M kinds of components each of the plurality of components recognized in the first time-series data is based on the fitting of the first time-series data with the second time-series data of each of the individual model fluorescence signals of each of the M kinds of components.

2. The analysis system according to claim 1, wherein the processor is configured to output third time-series data of a concentration of each of the plurality of components recognized in the first time-series data by fitting the second time-series data to the first time-series data.

3. The analysis system according to claim 2, wherein the storage device stores mobility difference data relating to a difference in mobility between the M kinds of components each of which is labeled with the different fluorescent substance, and
wherein the processor is configured to correct differences in mobility in the third time-series data based on the mobility difference data.

4. The analysis system according to claim 2, wherein the processor is configured to output fitting error data or fitting accuracy data relating to a difference between the first time-series data and a result of the fitting on each of the plurality of components.

5. The analysis system according to claim 4, further comprising:
a display coupled to the processor,
wherein the processor is configured to display, on the display, at least one of:
(i) the result of the fitting relating to each of the plurality of components,
(ii) fitting error data or fitting accuracy data relating to each of the plurality of components, and
(iii) the third time-series data.

6. The analysis system according to claim 1,
wherein the plurality of components are nucleic acid fragments of different lengths or of different compositions, and
wherein the chromatography is electrophoresis.

7. The analysis system according to claim 6,
wherein the plurality of components are DNA fragments prepared by a Sanger method using a target DNA as a template, wherein the DNA fragments comprise four kinds of DNA fragments respectively terminally labeled with four kinds of fluorescent substances according to terminal base species,
wherein the first time-series data is time-series data of fluorescence signals detected in three kinds or two kinds of wavelength bands, and
wherein the processor is configured to determine a base sequence of the target DNA.

8. The analysis system of claim 1,
wherein the fitting of the peaks of the first time-series data with peaks of the second time-series data is performed by changing a height and a time of each second time-series data of the individual model fluorescence signals.

9. An analysis method comprising:
separating a sample including a plurality of components by chromatography wherein the plurality of components comprise M kinds of components each of which is labeled with a different fluorescent substance, wherein the M is an integer greater than 1;
acquiring first time-series data of fluorescence signals detected in N kinds of wavelength bands for each of the different fluorescent substances, wherein N is an integer greater than 1 and M is greater than the N, in a state in which at least a portion of the plurality of components is not completely separated;
storing second time-series data of individual model fluorescence signals of each of the M kinds of components each of which is labeled with the different of fluorescent substance detected in the N kinds of wavelength bands, each second time-series data of the individual model fluorescence signals of each of the M kinds of components indicates a temporal change in fluorescence intensity in the N kinds of wavelength bands;
storing the acquired first time-series data having the detected fluorescence signals, the detected fluorescence signals including detected fluorescence signals of two or more of the M kinds of components in a space-time overlap;
performing fitting of peaks of the first time-series data with peaks of the second time-series data of each of the individual model fluorescence signals of each of the M kinds of components; and
determining which of the M kinds of components each of the plurality of components recognized in the first-time series data is based on the fitting of the first time-series data with the second time-series data of each of the individual model fluorescence signals of each of the M kinds of components.

10. The analysis method according to claim 9, further comprising:
outputting third time-series data of a concentration of each of the plurality of components recognized in the first time-series data by fitting the second time-series data to the first time-series data.

11. The analysis method according to claim 10, further comprising:
storing mobility difference data relating to a difference in mobility between the M kinds of components each of which is labeled with the different fluorescent substance,
wherein the determining includes correcting differences in mobility in the third time-series data based on the mobility difference data.

12. The analysis method according to claim 10,
wherein the determining includes outputting fitting error data or fitting accuracy data relating to a difference between the first time-series data and a result of the fitting on each of the plurality of components.

13. The analysis method according to claim 12, further comprising displaying at least one of:
(i) the result of the fitting relating to each of the plurality of components,
(ii) fitting error data or fitting accuracy data relating to each of the plurality of components, and
(iii) the third time-series data.

14. The analysis method according to claim 9,
wherein the plurality of components are nucleic acid fragments of different lengths or of different compositions, and
wherein the chromatography is electrophoresis.

15. The analysis method according to claim 14,
wherein the plurality of components are DNA fragments prepared by a Sanger method using a target DNA as a template, wherein the DNA fragments comprise four kinds of DNA fragments respectively terminally labeled with four kinds of fluorescent substances according to terminal base species,
wherein the first time-series data is time-series data of fluorescence signals detected in three kinds or two kinds of wavelength bands, and
wherein the determining includes determining a base sequence of the target DNA.

16. The analysis method of claim 9,
wherein the fitting of the peaks of the first time-series data with peaks of the second time-series data is performed by changing a height and a time of each second time-series data of the individual model fluorescence signals.

* * * * *